United States Patent
Shelton, IV

(10) Patent No.: US 12,096,971 B2
(45) Date of Patent: Sep. 24, 2024

(54) ELECTROSURGICAL INSTRUMENT WITH ELECTRICAL RESISTANCE MONITOR AT ROTARY COUPLING

(71) Applicant: Cilag GmbH International, Zug (CH)

(72) Inventor: Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 568 days.

(21) Appl. No.: 17/136,154

(22) Filed: Dec. 29, 2020

(65) Prior Publication Data

US 2022/0202476 A1 Jun. 30, 2022

(51) Int. Cl.
*A61B 18/14* (2006.01)
*A61B 18/00* (2006.01)
*A61B 34/37* (2016.01)

(52) U.S. Cl.
CPC .......... *A61B 18/1447* (2013.01); *A61B 34/37* (2016.02); *A61B 2018/00696* (2013.01); *A61B 2018/00791* (2013.01); *A61B 2018/00892* (2013.01)

(58) Field of Classification Search
None
See application file for complete search history.

(56) References Cited

U.S. PATENT DOCUMENTS

| | | | |
|---|---|---|---|
| 4,184,492 A | 1/1980 | Meinke et al. | |
| 5,312,401 A | 5/1994 | Newton et al. | |
| 7,070,420 B1 | 7/2006 | Wakefield et al. | |
| 7,354,440 B2 | 4/2008 | Truckai et al. | |
| 7,381,209 B2 | 6/2008 | Truckai et al. | |
| 7,762,958 B1 * | 7/2010 | Webler .................. | A61B 90/06 600/549 |

(Continued)

FOREIGN PATENT DOCUMENTS

| | | |
|---|---|---|
| EP | 2926752 A2 | 10/2015 |
| EP | 3417797 A1 | 12/2018 |

(Continued)

OTHER PUBLICATIONS

U.S. Appl. No. 17/136,137, entitled "Filter for Monopolar Surgical Instrument Energy Path," filed Dec. 29, 2020.

(Continued)

*Primary Examiner* — Sean W Collins
*Assistant Examiner* — Nora W Rhodes
(74) *Attorney, Agent, or Firm* — Frost Brown Todd LLP

(57) ABSTRACT

An apparatus includes a shaft assembly. A sliding electrical coupling provides electrical continuity between components of the shaft while permitting movement of a second shaft component relative to a first shaft component at the joint. An end effector is positioned at a distal end of the shaft assembly and is operable to engage tissue of a patient. A sensor is positioned adjacent to the joint and is configured to measure a joint parameter indicating a state of the sliding electrical coupling. The sensor transmits a first signal indicative of the measured joint parameter to a control module. The control module determines whether the measured joint parameter exceeds a maximum deviation from a predetermined value. When the measured joint parameter exceeds a maximum deviation from a predetermined value, the control module initiates a responsive action.

20 Claims, 13 Drawing Sheets

(56) References Cited

U.S. PATENT DOCUMENTS

| | | | |
|---|---|---|---|
| 8,663,220 B2 | 3/2014 | Wiener et al. | |
| 8,820,605 B2 | 9/2014 | Shelton, IV | |
| 9,125,662 B2 | 9/2015 | Shelton, IV | |
| 9,314,308 B2 | 4/2016 | Parihar et al. | |
| 9,949,785 B2 | 4/2018 | Price et al. | |
| 10,090,616 B1 | 10/2018 | Leimbach et al. | |
| 10,624,709 B2 | 4/2020 | Remm | |
| 10,639,038 B2 | 5/2020 | Scott et al. | |
| 10,813,640 B2 | 10/2020 | Adams et al. | |
| 10,835,307 B2 | 11/2020 | Shelton, IV et al. | |
| 10,842,523 B2 | 11/2020 | Shelton, IV et al. | |
| 2002/0128643 A1 | 9/2002 | Simpson et al. | |
| 2004/0206365 A1 | 10/2004 | Knowlton | |
| 2006/0041251 A1 | 2/2006 | Odell et al. | |
| 2006/0041252 A1 | 2/2006 | Odell et al. | |
| 2006/0079874 A1 | 4/2006 | Faller et al. | |
| 2007/0049919 A1 | 3/2007 | Lee, Jr. et al. | |
| 2007/0191713 A1 | 8/2007 | Eichmann et al. | |
| 2008/0200940 A1 | 8/2008 | Eichmann et al. | |
| 2009/0036884 A1 | 2/2009 | Gregg et al. | |
| 2010/0042097 A1 | 2/2010 | Newton et al. | |
| 2011/0034910 A1* | 2/2011 | Ross | A61B 17/072 340/5.1 |
| 2012/0292367 A1 | 11/2012 | Morgan et al. | |
| 2013/0123783 A1 | 5/2013 | Marczyk et al. | |
| 2014/0249557 A1* | 9/2014 | Koch, Jr. | A61B 90/98 606/170 |
| 2015/0313628 A1 | 11/2015 | Allen, IV | |
| 2015/0320481 A1 | 11/2015 | Cosman, Jr. et al. | |
| 2016/0143685 A1 | 5/2016 | Friedrichs | |
| 2016/0192980 A1 | 7/2016 | Newton et al. | |
| 2016/0296268 A1 | 10/2016 | Gee et al. | |
| 2017/0202591 A1 | 7/2017 | Shelton, IV et al. | |
| 2017/0202605 A1 | 7/2017 | Shelton, IV et al. | |
| 2017/0202608 A1 | 7/2017 | Shelton, IV et al. | |
| 2018/0012719 A1 | 1/2018 | Houbre et al. | |
| 2018/0078170 A1 | 3/2018 | Panescu et al. | |
| 2018/0132850 A1 | 5/2018 | Leimbach et al. | |
| 2018/0333185 A1* | 11/2018 | Asher | A61B 18/00 |
| 2019/0142492 A1 | 5/2019 | Kollmann et al. | |
| 2019/0189903 A1 | 6/2019 | Benedict et al. | |
| 2019/0201047 A1 | 7/2019 | Yates et al. | |
| 2019/0201075 A1 | 7/2019 | Shelton, IV et al. | |
| 2019/0201077 A1 | 7/2019 | Yates et al. | |
| 2019/0247680 A1 | 8/2019 | Mayer et al. | |
| 2019/0290269 A1 | 9/2019 | Shelton, IV et al. | |
| 2019/0290273 A1 | 9/2019 | Shelton, IV et al. | |
| 2019/0290308 A1 | 9/2019 | Worthington et al. | |
| 2020/0069365 A1 | 3/2020 | Harlev et al. | |
| 2020/0078075 A1 | 3/2020 | Katsuragi | |
| 2020/0384502 A1 | 12/2020 | Downey et al. | |
| 2021/0059709 A1 | 3/2021 | Black et al. | |

FOREIGN PATENT DOCUMENTS

| | | |
|---|---|---|
| EP | 3420918 A1 | 1/2019 |
| EP | 3461447 A1 | 4/2019 |
| EP | 3479787 A1 | 5/2019 |
| EP | 3542733 A1 | 9/2019 |
| WO | WO 1992/008417 A1 | 5/1992 |
| WO | WO 2018/165425 A1 | 9/2018 |
| WO | WO 2019/130111 A1 | 7/2019 |
| WO | WO 2020/051462 A1 | 3/2020 |

OTHER PUBLICATIONS

U.S. Appl. No. 17/136,139, entitled "Electrosurgical Instrument System with Parasitic Energy Loss Monitor," filed Dec. 29, 2020.

U.S. Appl. No. 17/136,141, entitled "Energized Surgical Instrument System with Multi-Generator Output Monitoring," filed Dec. 29, 2020.

U.S. Appl. No. 17/136,145, entitled "Electrosurgical Instrument with Shaft Voltage Monitor," filed Dec. 29, 2020.

U.S. Appl. No. 17/136,158, entitled "Electrosurgical Instrument with Modular Component Contact Monitoring," filed Dec. 29, 2020.

International Search Report and Written Opinion dated May 17, 2022, for International Application No. PCT/IB2021/062411, 20 pages.

International Search Report and Written Opinion dated Mar. 22, 2022, for International Application No. PCT/IB2021/062413, 13 pages.

International Search Report and Written Opinion dated Mar. 24, 2022, for International Application No. PCT/IB2021/062414, 17 pages.

International Search Report and Written Opinion dated Mar. 24, 2022, for International Application No. PCT/IB2021/062416, 16 pages.

International Search Report and Written Opinion dated Mar. 30, 2022, for International Application No. PCT/IB2021/062417, 17 pages.

International Search Report and Written Opinion dated Apr. 7, 2022, for International Application No. PCT/IB2021/062418, 13 pages.

* cited by examiner

ELECTROSURGICAL INSTRUMENT WITH ELECTRICAL RESISTANCE MONITOR AT ROTARY COUPLING

BACKGROUND

A variety of ultrasonic surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein, in its entirety; U.S. Pub. No. 2007/0191713, entitled "Ultrasonic Device for Cutting and Coagulating," published Aug. 16, 2007, now abandoned, the disclosure of which is incorporated by reference herein, in its entirety; and U.S. Pub. No. 2008/0200940, entitled "Ultrasonic Device for Cutting and Coagulating," published Aug. 21, 2008, now abandoned, the disclosure of which is incorporated by reference herein, in its entirety.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein, in its entirety; U.S. Pat. No. 7,381,209, entitled "Electrosurgical Instrument," issued Jun. 3, 2008, the disclosure of which is incorporated by reference herein, in its entirety.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein, in its entirety; and U.S. Pat. No. 8,663,220, entitled "Ultrasonic Electrosurgical Instruments," issued Mar. 4, 2014, the disclosure of which is incorporated by reference herein, in its entirety.

In some scenarios, it may be preferable to have surgical instruments grasped and manipulated directly by the hand or hands of one or more human operators. In addition, or as an alternative, it may be preferable to have surgical instruments controlled via a robotic surgical system. Examples of robotic surgical systems and associated instrumentation are disclosed in U.S. Pat. No. 10,624,709, entitled "Robotic Surgical Tool with Manual Release Lever," issued on Apr. 21, 2020, the disclosure of which is incorporated by reference herein, in its entirety; U.S. Pat. No. 9,314,308, entitled "Robotic Ultrasonic Surgical Device With Articulating End Effector," issued on Apr. 19, 2016, the disclosure of which is incorporated by reference herein, in its entirety; U.S. Pat. No. 9,125,662, entitled "Multi-Axis Articulating and Rotating Surgical Tools," issued Sep. 8, 2015, the disclosure of which is incorporated by reference herein, in its entirety; U.S. Pat. No. 8,820,605, entitled "Robotically-Controlled Surgical Instruments," issued Sep. 2, 2014, the disclosure of which is incorporated by reference herein, in its entirety; U.S. Pub. No. 2019/0201077, entitled "Interruption of Energy Due to Inadvertent Capacitive Coupling," published Jul. 4, 2019, issued as U.S. Pat. No. 11,291,495 on Apr. 5, 2022, the disclosure of which is incorporated by reference herein, in its entirety; U.S. Pub. No. 2012/0292367, entitled "Robotically-Controlled End Effector," published on Nov. 11, 2012, now abandoned, the disclosure of which is incorporated by reference herein, in its entirety; and U.S. patent application Ser. No. 16/556,661, entitled "Ultrasonic Surgical Instrument with a Multi-Planar Articulating Shaft Assembly," filed on Aug. 30, 2019, issued as U.S. Pat. No. 11,6990,642 on Jul. 4, 2023, the disclosure of which is incorporated by reference herein, in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
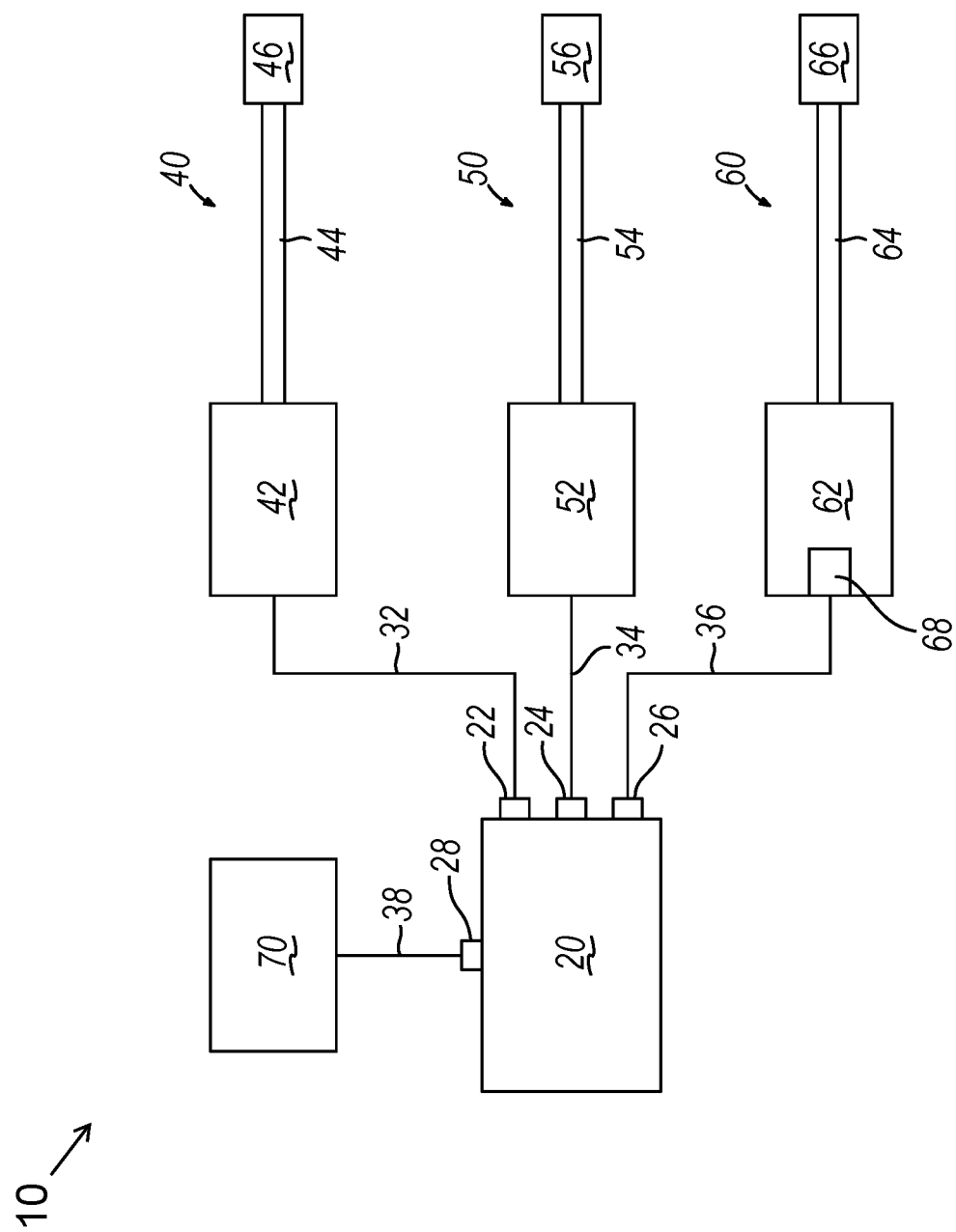
FIG. 1 depicts a schematic view of an example of a robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "top," "bottom," "above," and "below," are used with respect to the examples and associated figures and are not intended to unnecessarily limit the invention described herein.

I. EXAMPLE OF A ROBOTIC SURGICAL SYSTEM

As noted above, in some surgical procedures, it may be desirable to utilize a robotically controlled surgical system. Such a robotically controlled surgical system may include one or more surgical instruments that are controlled and driven robotically via one or more users that are either in the same operating room or remote from the operating room. FIG. 1 illustrates on example of various components that may be incorporated into a robotic surgical system (10). System (10) of this example includes a console (20), a monopolar RF electrosurgical instrument (40), a bipolar RF electrosurgical instrument (50), and an ultrasonic surgical instrument (60). While FIG. 1 shows all three instruments (40, 50, 60) coupled with console (20) at the same time, there may be usage scenarios where only one or two of instruments (40, 50, 60) coupled with console (20) at the same time. In addition, there may be usage scenarios where various other instruments are coupled with console (20) in addition, or as an alternative to, one or more of instruments (40, 50, 60) being coupled with console (20).

Monopolar RF electrosurgical instrument (40) of the present example includes a body (42), a shaft (44) extending distally from body (42), and an end effector (46) at the distal end of shaft (44). Body (42) is configured to couple with a robotic arm (not shown in FIG. 1) of system (10), such that the robotic arm is operable to position and orient monopolar RF electrosurgical instrument (40) in relation to a patient. In versions where monopolar RF electrosurgical instrument (40) includes one or more mechanically driven components (e.g., jaws at end effector (46), articulating sections of shaft (44), rotating sections of shaft (44), etc.), body (42) may include various components that are operable to convert one or more mechanical drive inputs from the robotic arm into motion of the one or more mechanically driven components of monopolar RF electrosurgical instrument (40).

As also shown in FIG. 1, body (42) is coupled with a corresponding port (22) of console (20) via a cable (32). Console (20) is operable to provide electrical power to monopolar RF electrosurgical instrument (40) via port (22) and cable (32). In some versions, port (22) is dedicated to driving monopolar RF electrosurgical instruments like monopolar RF electrosurgical instrument (40). In some other versions, port (22) is operable to drive various kinds of instruments (e.g., including instruments (50, 60), etc.). In some such versions, console (20) is operable to automatically detect the kind of instrument (40, 50, 60) that is coupled with port (22) and adjust the power profile to port (22) accordingly. In addition, or in the alternative, console (20) may adjust the power profile to port (22) based on a selection made by an operator via console (20), manually identifying the kind of instrument (40, 50, 60) that is coupled with port (22).

Shaft (44) is operable to support end effector (46) and provides one or more wires or other paths for electrical communication between base (42) and end effector (46). Shaft (44) is thus operable to transmit electrical power from console (20) to end effector (46). Shaft (44) may also include various kinds of mechanically movable components, including but not limited to rotating segments, articulating sections, and/or other kinds of mechanically movable components as will be apparent to those skilled in the art in view of the teachings herein.

End effector (46) of the present example includes an electrode that is operable to apply monopolar RF energy to tissue. Such an electrode may be incorporated into a sharp blade, a needle, a flat surface, some other atraumatic structure, or any other suitable kind of structure as will be apparent to those skilled in the art in view of the teachings herein. End effector (46) may also include various other kinds of components, including but not limited to grasping jaws, etc.

System (10) of this example further includes a ground pad (70) that is coupled with a corresponding port (28) of console (20) via a cable (38). In some versions, ground pad (70) is incorporated into a patch or other structure that is adhered to the skin of the patient (e.g., on the thigh of the patient). In some other versions, ground pad (70) is placed under the patient (e.g., between the patient and the operating table). In either case, ground pad (70) may serve as a return path for monopolar RF energy that is applied to the patient via end effector (46). In some versions, port (28) is a dedicated ground return port. In some other versions, port (28) is a multi-purpose port that is either automatically designated as a ground return port upon console (20) detecting the coupling of ground pad (70) with port (28) or manually designated as a ground return port via an operator using a user input feature of console (20).

Bipolar RF electrosurgical instrument (50) of the present example includes a body (52), a shaft (54) extending distally from body (52), and an end effector (56) at the distal end of shaft (54). Each of these components (52, 54, 56) may be configured and operable in accordance with the above description of corresponding components (42, 44, 46) of monopolar RF electrosurgical instrument (50), except that end effector (56) of this example is operable to apply bipolar RF energy to tissue. Thus, end effector (56) includes at least two electrodes, with those two electrodes being configured to cooperate with each other to apply bipolar RF energy to tissue. Bipolar RF electrosurgical instrument (50) is coupled with console (20) via a cable (34), which is further coupled with a port (24) of console (20). Port (24) may be dedicated to powering bipolar RF electrosurgical instruments. Alternatively, port (24) or may be a multi-purpose port whose output is determined based on either automatic detection of bipolar RF electrosurgical instrument (50) or operator selection via a user input feature of console (20).

Ultrasonic surgical instrument (60) of the present example includes a body (62), a shaft (64) extending distally from body (62), and an end effector (66) at the distal end of shaft (64). Each of these components (62, 64, 66) may be configured and operable in accordance with the above description of corresponding components (42, 44, 46) of monopolar RF electrosurgical instrument (50), except that end effector (66) of this example is operable to apply ultrasonic energy to tissue. Thus, end effector (66) includes an ultrasonic blade or other ultrasonically vibrating element. In addition, base (62) includes an ultrasonic transducer (68) that is operable to generate ultrasonic vibrations in response to electrical power, while shaft (64) includes an acoustic waveguide that is operable to communicate the ultrasonic vibrations from transducer (68) to end effector (66).

Ultrasonic surgical instrument (60) is coupled with console (20) via a cable (36), which is further coupled with a port (26) of console (20). Port (26) may be dedicated to powering ultrasonic electrosurgical instruments. Alternatively, port (26) or may be a multi-purpose port whose output is determined based on either automatic detection of ultrasonic instrument (60) or operator selection via a user input feature of console (20).

While FIG. 1 shows monopolar RF, bipolar RF, and ultrasonic capabilities being provided via three separate, dedicated instruments (40, 50, 60), some versions may include an instrument that is operable to apply two or more of monopolar RF, bipolar RF, or ultrasonic energy to tissue. In other words, two or more of such energy modalities may be incorporated into a single instrument. Examples of how such different modalities may be integrated into a single instrument are described in U.S. Pub. No. 2017/0202591, entitled "Modular Battery Powered Handheld Surgical Instrument with Selective Application of Energy Based on Tissue Characterization," published Jul. 20, 2017, issued as U.S. Pat. No. 11,229,471 on Jan. 25,2022, the disclosure of which is incorporated by reference herein, in its entirety. Other examples will be apparent to those skilled in the art in view of the teachings herein.

Figure 2:
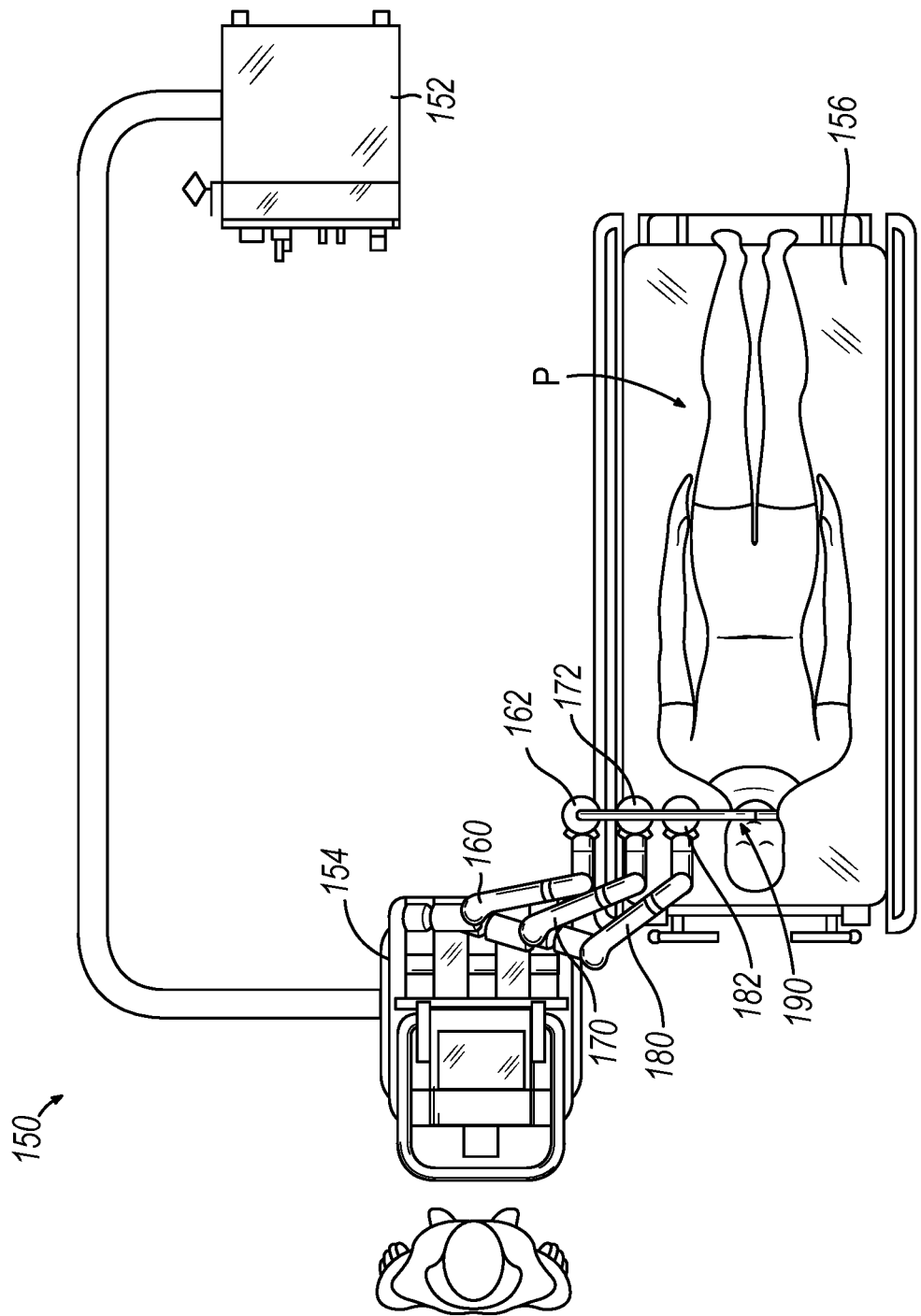
FIG. 2 depicts a schematic view of an example of a robotic surgical system being used in relation to a patient.

FIG. 2 shows an example of a robotic surgical system (150) in relation to a patient (P) on a table (156). System (150) of this example includes a control console (152) and a drive console (154). Console (152) is operable to receive user inputs from an operator; while drive console (154) is operable to convert those user inputs into motion of a set of robotic arms (160, 170, 180). In some versions, consoles (152, 154) collectively form an equivalent to console (20) described above. While consoles (152, 154) are shown as separate units in this example, consoles (152, 154) may in fact be combined as a single unit in some other examples.

Robotic arms (160, 170, 180) extend from drive console (154) in this example. In some other versions, robotic arms (160, 170, 180) are integrated into table (156) or some other structure. Each robotic arm (160, 170, 180) has a corresponding drive interface (162, 172, 182). In this example, three drive interfaces (162, 172, 182) are coupled with one single instrument assembly (190). In some other scenarios, each drive interface (162, 172, 182) is coupled with a separate respective instrument. By way of example only, a drive interface (162, 172, 182) may couple with a body of an instrument, like bodies (42, 52, 62) of instruments (40, 50, 60) described above. In any case, robotic arms (160, 170, 180) may be operable to move instrument (40, 50, 60, 190) in relation to the patient (P) and actuate any mechanically driven components of instrument (40, 50, 60, 190). Robotic arms (160, 170, 180) may also include features that provide a pathway for communication of electrical power to instrument (40, 50, 60, 190). For instance, cables (32, 34, 36) may be at least partially integrated into robotic arms (160, 170, 180). In some other versions, robotic arms (160, 170, 180) may include features to secure but not necessarily integrate cables (32, 34, 36). As yet another variation, cables (32, 34, 36) may simply stay separate from robotic arms (160, 170, 180). Other suitable features and arrangements that may be used to form robotic surgical systems (10, 150) will be apparent to those skilled in the art in view of the teachings herein.

In robotic surgical systems like robotic surgical systems (10, 150), each port (22, 24, 26, 28) may have a plurality of electrical features providing inputs and outputs between console (20, 152) and robotic arms (160, 170, 180) and/or instruments (40, 50, 60, 190). These electrical features may include sockets, pins, contacts, or various other features that are in close proximity with each other. In some scenarios, this proximity may provide a risk of power or signals undesirably crossing from one electrical feature to another electrical feature, which may cause equipment failure, equipment damage, sensor errors, and/or other undesirable results. In addition, or in the alternative, this proximity may provide a risk of generating electrical potentials between proximate components or creating capacitive couplings between electrical features. Such capacitive coupling may provide undesirable results such as power reductions, signal reductions, signal interference, patient injuries, and/or other undesirable results. It may therefore be desirable to provide features to prevent or otherwise address such occurrences at ports (22, 24, 26, 28).

Similarly, each robotic arm (160, 170, 180), each cable (32, 34, 36, 38), and/or each instrument (40, 50, 60, 190) may include a plurality of wires, traces in rigid or flexible circuits, and other electrical features that are in close proximity with each other. Such electrical features may also be in close proximity with other components that are not intended to provide pathways for electrical communication but are nevertheless formed of an electrically conductive material. Such electrically conductive mechanical features may include moving components (e.g., drive cables, drive bands, gears, etc.) or stationary components (e.g., chassis or frame members, etc.). This proximity may provide a risk of power or signals undesirably crossing from one electrical feature to another electrical feature and/or from one electrical feature to an electrically conductive mechanical feature, which may cause equipment failure, equipment damage, sensor errors, and/or other undesirable results. In addition, or in the alternative, this proximity may provide a risk of generating electrical potentials between proximate components or creating capacitive couplings between electrical features and/or between an electrical feature and an electrically conductive mechanical feature. Such capacitive coupling may provide undesirable results such as power reductions, signal reductions, signal interference, patient injuries, and/or other undesirable results. It may therefore be desirable to provide features to prevent or otherwise address such occurrences within robotic arms (160, 170, 180), within cables (32, 34, 36, 38), and/or within instruments (40, 50, 60, 190).

II. EXAMPLE OF HANDHELD SURGICAL INSTRUMENT

Figure 3:
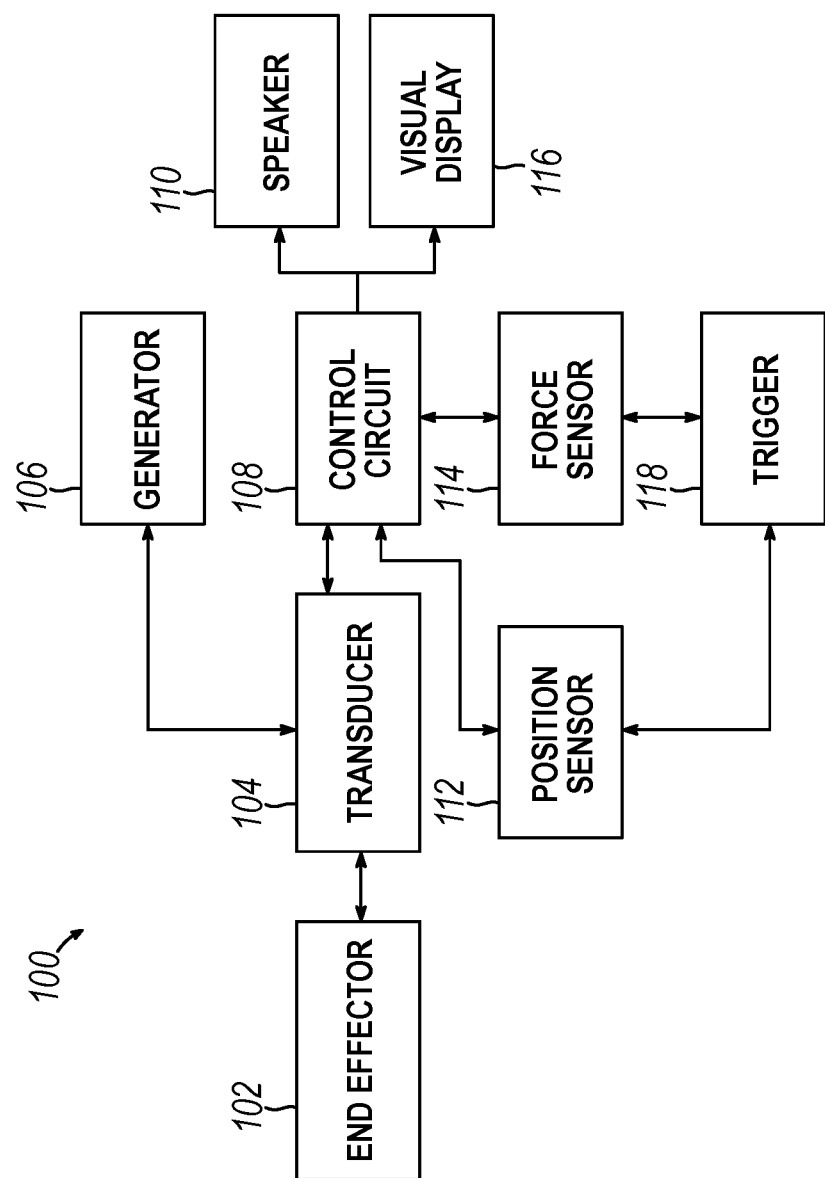
FIG. 3 depicts a schematic view of examples of components that may be incorporated into a surgical instrument.

In some procedures, an operator may prefer to use a handheld surgical instrument in addition to, or in lieu of, using a robotic surgical system (10, 150). FIG. 3 illustrates an example of various components that may be integrated into a handheld surgical instrument (100). In addition to the following teachings, instrument (200) may be constructed and operable in accordance with at least some of the teachings of U.S. Pub. No. 2017/0202608, entitled "Modular Battery Powered Handheld Surgical Instrument Containing Elongated Multi-Layered Shaft," published Jul. 20, 2017, issued as U.S. Pat. No. 10,835,307 on Nov. 17, 2020, the disclosure of which is incorporated by reference herein, in its entirety; and/or various other references cited herein. Instrument (100) of this example includes an end effector (102), an ultrasonic transducer (104), a power generator (106), a control circuit (108), a speaker (110), a position sensor (112), a force sensor (114), a visual display (116), and a trigger (118). In some versions, end effector (102) is disposed at a distal end of a shaft (not shown in FIG. 3), while the other components (104, 106, 108, 110, 112, 114, 116, 118) are incorporated into a handle assembly (not shown in FIG. 3) at the proximal end of the shaft. Some variations may also provide some of components (104, 106, 108, 110, 112, 114, 116, 118) in a separate piece of capital equipment. For instance, power generator (106), speaker (110), and/or visual display (116) may be incorporated into a separate piece of capital equipment that is coupled with instrument (100).

End effector (102) may be configured and operable like end effectors (46, 56, 66) described above, such that end effector (102) may be operable to apply monopolar RF energy, bipolar RF energy, or ultrasonic energy to tissue. Transducer (104) may be configured and operable like transducer (68). Generator (106) may be operable to provide electrical power as needed to drive transducer (68) and/or to provide RF energy via end effector (102). In versions where generator (106) is integrated into a handle assembly of instrument (106), generator (106) may comprise one or more battery cells, etc. Control circuit (108) may include one or more microprocessors and/or various other circuitry components that may be configured to provide signal processing and other electronic aspects of operability of instrument (100). Position sensor (112) may be configured to sense the position and/or orientation of instrument (102). In some versions, control circuit (108) is configured to vary the operability of instrument (102) based on data from position sensor (112). Force sensor (114) is operable to sense one or more force parameters associated with usage of instrument (100). Such force parameters may include force being applied to instrument (100) by the operator, force applied to tissue by end effector (102), or other force parameters as will be apparent to those skilled in the art in view of the teachings herein. In some versions, control circuit (108) is configured to vary the operability of instrument (102) based on data from force sensor (114). In some versions, one or both of sensors (112, 114) may be incorporated into end effector (102). In addition, or in the alternative, one or both of sensors (112, 114) may be incorporated into a shaft assembly (not shown) of instrument (100). Variations of instrument (100) may also incorporate various other kinds of sensors (e.g., in addition to or in lieu of sensors (112, 114) in end effector (102), in the shaft assembly, and/or elsewhere within instrument (100).

Trigger (118) is operable to control an aspect of operation of end effector (102), such as movement of a pivoting jaw, translation of a cutting blade, etc. Speaker (110) and visual display (116) are operable to provide audible and visual feedback to the operator relating to operation of instrument (100). The above-described components (102, 104, 106, 108, 110, 112, 114, 116, 118) of instrument (100) are illustrative examples, such that components (102, 104, 106, 108, 110, 112, 114, 116, 118) may be varied, substituted, supplemented, or omitted as desired.

Figure 4:
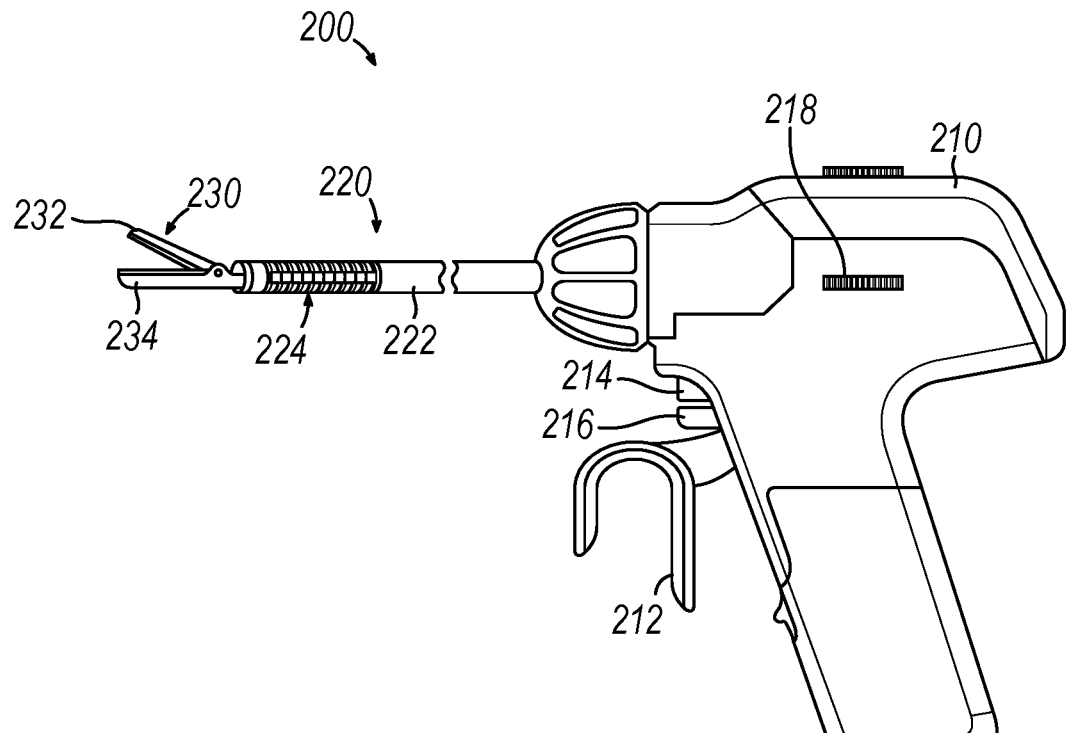
FIG. 4 depicts a side elevation view of an example of a handheld surgical instrument.

FIG. 4 shows an example of a form that instrument (100) may take. In particular, FIG. 4 shows a handheld instrument (200). In addition to the following teachings, instrument (200) may be constructed and operable in accordance with at least some of the teachings of U.S. Pub. No. 2017/0202591, issued as U.S. Pat. No. 11,229,471 on Jan. 25, 2022, the disclosure of which is incorporated by reference herein, in its entirety; and/or various other references cited herein. In the present example, instrument (200) includes a handle assembly (210), a shaft assembly (220), and an end effector (230). Handle assembly (210) includes a pivoting trigger (212), a first trigger button (214), a second trigger button (216), and an articulation control (218). Shaft assembly (220) includes a rigid shaft portion (222) and an articulation section (224). End effector (230) is distal to articulation section (224) and includes an upper jaw (232) and a lower jaw (234).

By way of example only, handle assembly (210) may include one or more of the above-described components (104, 106, 108, 110, 112, 114, 116, 118). Trigger (212) may be operable to drive upper jaw (232) to pivot toward lower jaw (234) (e.g., to grasp tissue between haws (232, 234)). Trigger buttons (214, 216) may be operable to activate delivery of energy (e.g., RF energy and/or ultrasonic energy) via end effector (230). Articulation control (218) is operable to drive deflection of shaft assembly (220) at articulation section (224), thereby driving lateral deflection of end effector (230) away from or toward the central longitudinal axis defined by rigid shaft portion (222). End effector (230) may include one or more electrodes that is/are operable to apply monopolar and/or bipolar RF energy to tissue. In addition, or in the alternative, end effector (230) may include an ultrasonic blade that is operable to apply ultrasonic energy to tissue. In some versions, end effector (230) is operable to apply two or more of monopolar RF energy, bipolar RF energy, or ultrasonic energy to tissue. Other suitable features and functionalities that may be incorporated into end effector (230) will be apparent to those skilled in the art in view of the teachings herein.

Instruments (150, 200) may include a plurality of wires, traces in rigid or flexible circuits, and other electrical features that are in close proximity with each other. Such electrical features may be located within handle assembly (210), within shaft assembly (220), and/or in end effector (230). Such electrical features may also be in close proximity with other components that are not intended to provide pathways for electrical communication but are nevertheless formed of an electrically conductive material. Such electrically conductive mechanical features may include moving components (e.g., drive cables, drive bands, gears, etc.) or stationary components (e.g., chassis or frame members, etc.). This proximity may provide a risk of power or signals undesirably crossing from one electrical feature to another electrical feature and/or from one electrical feature to an electrically conductive mechanical feature, which may cause equipment failure, equipment damage, sensor errors, patient injuries, and/or other undesirable results. In addition, or in the alternative, this proximity may provide a risk of generating electrical potentials between proximate components or creating capacitive couplings between electrical features and/or between an electrical feature and an electrically conductive mechanical feature. Such capacitive coupling may provide undesirable results such as power reductions, signal reductions, signal interference, and/or other undesirable results. It may therefore be desirable to provide features to prevent or otherwise address such occurrences within instruments (150, 200).

III. FURTHER EXAMPLES OF SURGICAL INSTRUMENT COMPONENTS

The following description relates to examples of different features that may be incorporated into any of the various instruments (40, 50, 60, 100, 190, 200) described above. While these examples are provided separate from each other, the features described in any of the following examples may be combined with the features described in other examples described below. Thus, the below-described features may be combined in various permutations as will be apparent to those skilled in the art in view of the teachings herein. Similarly, various ways in which the below-described features may be incorporated into any of the various instruments (40, 50, 60, 100, 190, 200) described above will be apparent to those skilled in the art in view of the teachings herein. The below-described features may be incorporated into robotically controlled surgical instruments (40, 50, 60, 190) and/or handheld surgical instruments (100, 200).

A. Example of Ultrasonic End Effector

Figure 5:
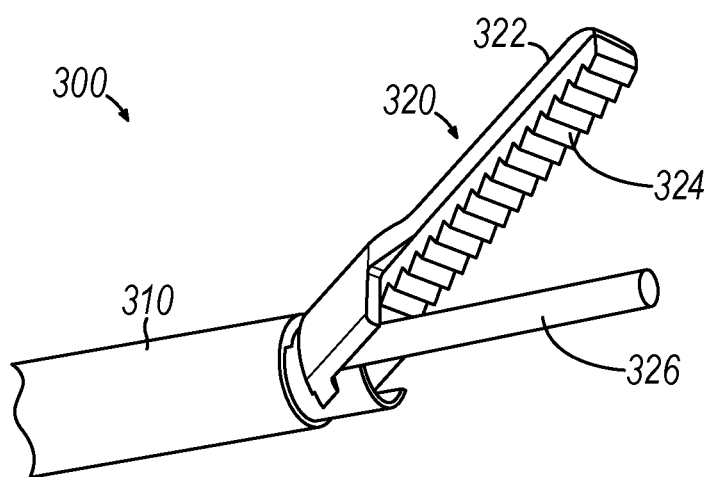
FIG. 5 depicts a perspective view of an example of an end effector that is operable to apply ultrasonic energy to tissue.

FIG. 5 shows a portion of an example of an ultrasonic instrument (300), including a shaft assembly (310) and an end effector (320). End effector (320) includes an upper jaw (322) and an ultrasonic blade (326). Upper jaw (322) is operable to pivot toward ultrasonic blade (326) to thereby compress tissue between a clamp pad (324) of upper jaw (322) and ultrasonic blade (326). When ultrasonic blade (326) is activated with ultrasonic vibrations, ultrasonic blade (326) may sever and seal tissue compressed against clamp pad (324). By way of example only, end effectors (66, 102, 230) may be configured and operable similar to end effector (320).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (300), such risks may occur with respect to an acoustic waveguide in shaft assembly (310) leading to ultrasonic blade (326), as the acoustic waveguide may be formed of an electrically conductive material. In addition, instrument (300) may include one or more sensors in shaft assembly (310) and/or end effector (320); and may also include one or more electrodes and/or other electrical features in end effector (320). Other components of instrument (350) that may present the above-described risks will be apparent to those skilled in the art in view of the teachings herein.

B. Example of Bipolar RF End Effector

Figure 6:
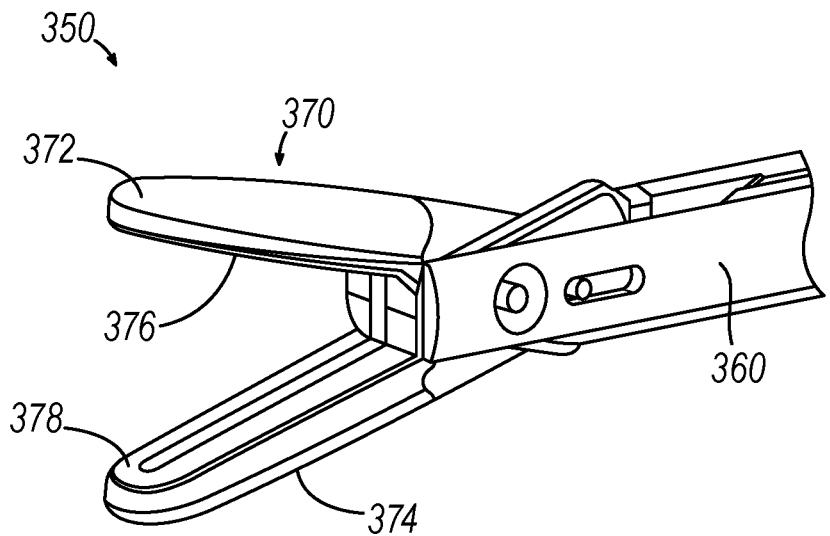
FIG. 6 depicts a perspective view of an example of an end effector that is operable to apply bipolar RF energy to tissue.

FIG. 6 shows a portion of an example of a bipolar RF instrument (350), including a shaft assembly (360) and an end effector (370). End effector (370) includes an upper jaw (372) and a lower jaw (374). Jaws (372, 374) are pivotable toward and away from each other. Upper jaw (372) includes a first electrode surface (376) while lower jaw (374) includes a second electrode surface (378). When tissue is compressed between jaws (372, 374), electrode surfaces (376, 378) may be activated with opposing polarities to thereby apply bipolar RF energy to the tissue. This bipolar RF energy may seal the compressed tissue. In some versions, end effector (370) further includes a translating knife member (not show) that is operable to sever tissue that is compressed between jaws (372, 374). Some variations of end effector (370) may also be operable to cooperate with a ground pad (e.g., ground pad (70)) to apply monopolar RF energy to tissue, such as by only activating one electrode surface (376, 378) or by activating both electrode surfaces (376, 378) at a single polarity. By way of example only, end effectors (64, 102, 230) may be configured and operable similar to end effector (370).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (350), such risks may occur with respect to electrode surface (376, 378) and the wires or other electrical features that extend along shaft assembly (360) to reach electrode surfaces (376, 378). In addition, instrument (350) may include one or more sensors in shaft assembly (360) and/or end effector (370); and may also include one or more electrodes and/or other electrical features in end effector (370). Other components of instrument (350) that may present the above-described risks will be apparent to those skilled in the art in view of the teachings herein.

C. Example of Monopolar Surgical Instrument Features

Figure 7:
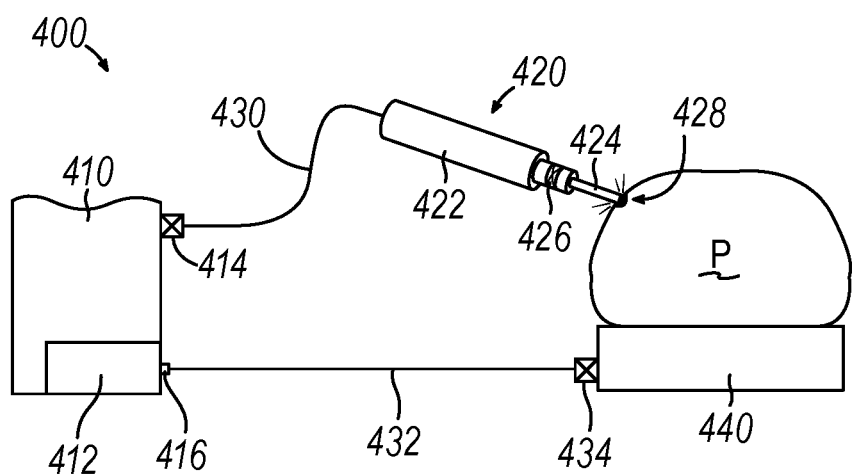
FIG. 7 depicts a schematic view of an example of a surgical instrument that is operable to apply monopolar RF energy to tissue.

FIG. 7 shows an example of a monopolar RF energy delivery system (400) that includes a power generator (410), a delivery instrument (420), and a ground pad assembly (440). In addition to the following teachings, instrument (420) may be constructed and operable in accordance with at least some of the teachings of U.S. Pub. No. 2019/0201077, issued as U.S. Pat. No. 11,291,495 on Apr. 5, 2022, the disclosure of which is incorporated by reference herein, in its entirety; and/or various other references cited herein. Power generator (410) may be operable to deliver monopolar RF energy to instrument (420) via a cable (430), which is coupled with power generator (410) via a port (414). In some versions, port (414) includes an integral sensor. By way of example only, such a sensor in port (414) may be configured to monitor whether excess or inductive energy is radiating from power generator (410) and/or other characteristics of energy being delivered from power generator (410) via port (414). Instrument (420) includes a body (422), a shaft (424), a sensor (426), and a distal electrode (428) that is configured to contact a patient (P) and thereby apply monopolar RF energy to the patient (P). By way of example only, sensor (426) may be configured to monitor whether excess or inductive energy is radiating from instrument (420). Based on signals from sensor (426), a control module in power generator (410) may passively throttle the ground return from ground pad assembly (440) based on data from sensor (426).

In some versions, ground pad assembly (440) comprises one or more resistive continuity ground pads that provide direct contact between the skin of the patient (P) and one or more metallic components of the ground pad. In some other versions, ground pad assembly (440) comprises a capacitive coupling ground pad that includes a gel material that is interposed between the patient (P) and the ground return plate. In the present example, ground pad assembly (440) is positioned under the patient (P) and is coupled to of power generator (410) via a cable (432) via ports (416, 434). Either or both of ports (416, 434) may include an integral sensor. By way of example only, such a sensor in either or both of ports (416, 434) may be configured to monitor whether excess or inductive energy is radiating from ground pad assembly (440).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (420), such risks may occur with respect to sensor (426), distal electrode (428), and/or any other electrical components in instrument (420). Other components of instrument (420) that may present the above-described risks will be apparent to those skilled in the art in view of the teachings herein. Such risks may be greater in versions instrument (420) that are dedicated to providing monopolar RF energy than in the context of bipolar RF instruments such as instrument (350) because a dedicated monopolar RF instrument may lack a ground return path that might otherwise prevent or mitigate the above risks.

D. Example of Articulation Section in Shaft Assembly

Figure 8:
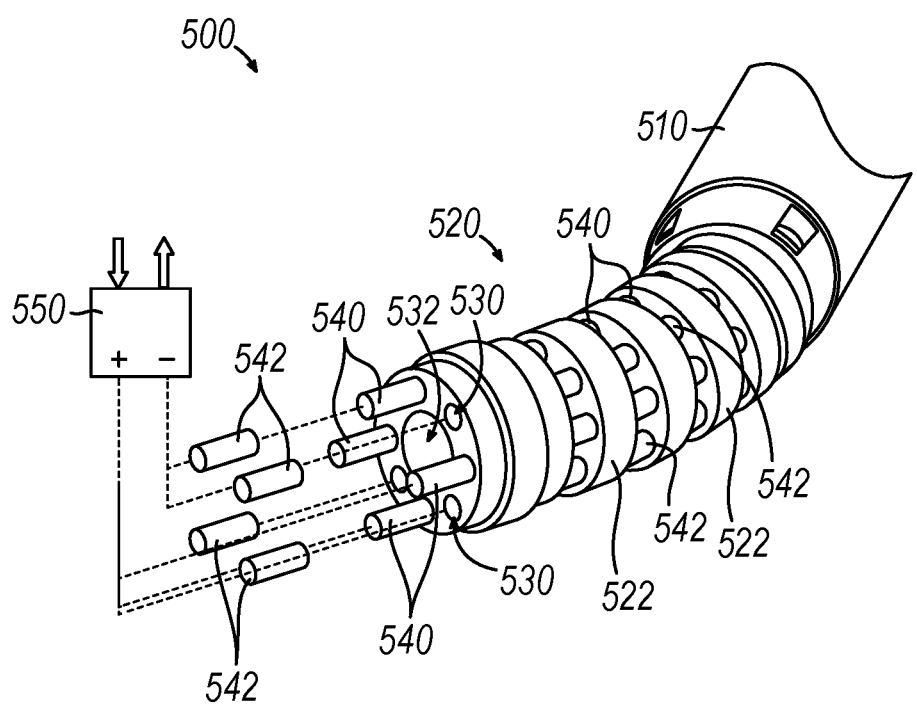
FIG. 8 depicts a perspective view of an example of an articulation section that may be incorporated into a shaft assembly of a surgical instrument.

FIG. 8 illustrates a portion of an instrument (500) that includes a shaft (510) with an articulation section (520). In addition to the following teachings, instrument (500) may be constructed and operable in accordance with at least some of the teachings of U.S. Pub. No. 2017/0202591, issued as U.S. Pat. No. 11,229,471 on Jan. 25, 2022, the disclosure of which is incorporated by reference herein, in its entirety; and/or various other references cited herein. In the present example, an end effector (550) is positioned at the distal end of articulation section (520). Articulation section (520) includes a plurality of segments (522) and is operable to laterally deflect end effector (550) away from and toward the central longitudinal axis of shaft (510). A plurality of wires (540) extend through shaft (510) and along articulation section (520) to reach end effector (550) and thereby deliver electrical power to end effector (550). By way of example only, end effector (550) may be operable to deliver monopolar and/or bipolar RF energy to tissue as described herein. A plurality of push-pull cables (542) also extend through articulation section (520). Push-pull cables (542) may be coupled with an actuator (e.g., similar to articulation control (218)) to drive articulation of articulation section (520). Segments (522) are configured to maintain separation between, and provide structural support to, wires (540) and push-pull cables (542) along the length of articulation section (520). Articulation section (520) of this example also defines a central passageway (532). By way of example only, central passageway (532) may accommodate an acoustic waveguide (e.g., in variations where end effector (550) further includes an ultrasonic blade), may provide a path for fluid communication, or may serve any other suitable purpose. Alternatively, central passageway (532) may be omitted.

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (500), such risks may occur with respect to wires (540) and/or push-pull cables (542). In addition, instrument (500) may include one or more sensors in shaft assembly (510) and/or end effector (550); and may also include one or more electrodes and/or other electrical features in end effector (550). Other components of instrument (500) that may present the above-described risks will be apparent to those skilled in the art in view of the teachings herein.

E. Example of Wiring to End Effector

Figure 9:
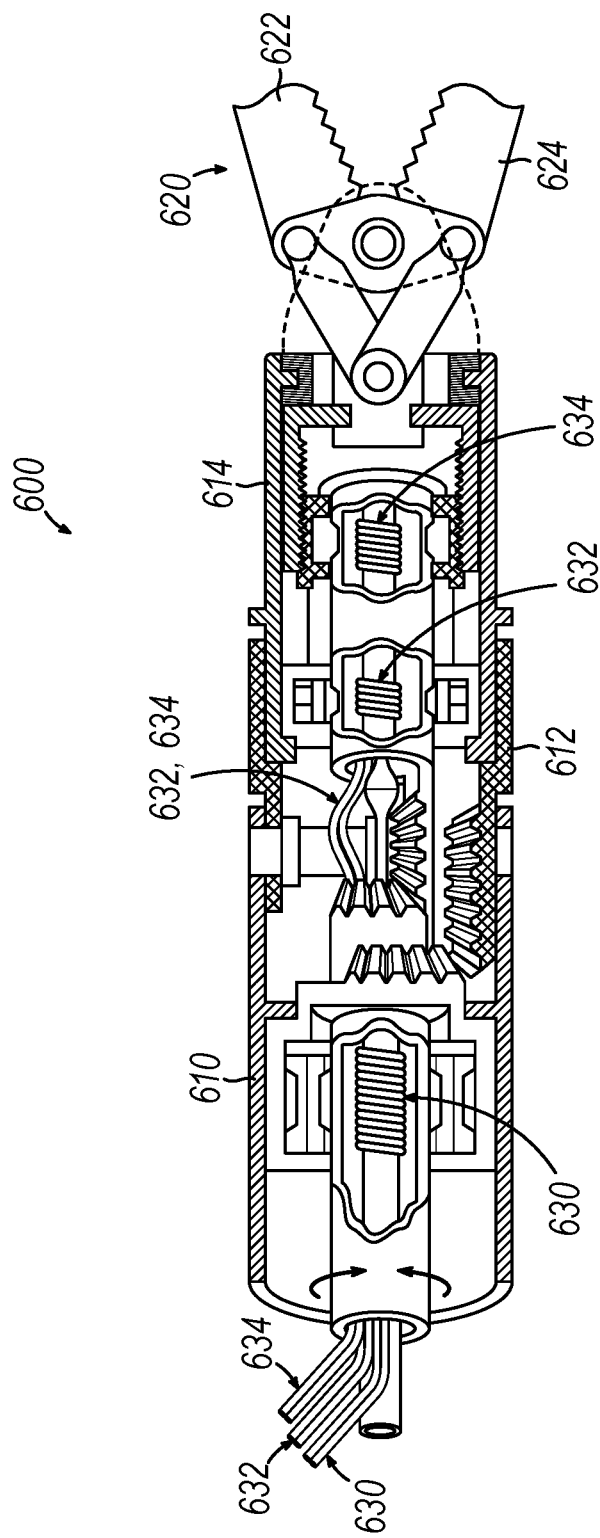
FIG. 9 depicts a side elevation view of a portion of a shaft assembly that may be incorporated into a surgical instrument, with housing components of the shaft being shown in cross-section to reveal internal components of the shaft.

FIG. 9 illustrates a portion of an instrument (600) that includes a shaft (610) with n first articulating segment (612) and a second articulating segment (614). In addition to the following teachings, instrument (600) may be constructed and operable in accordance with at least some of the teachings of U.S. Pub. No. 2017/0202605, entitled "Modular Battery Powered Handheld Surgical Instrument and Methods Therefor," published Jul. 20, 2017, issued as U.S. Pat. No. 10,842,253, the disclosure of which is incorporated by reference herein, in its entirety; and/or various other references cited herein. In the present example, end effector (620) is positioned at the distal end of second articulating segment (614). End effector (620) of this example includes a pair of jaws (622, 624) that are operable to pivot toward and away from each other to grasp tissue. In some versions, one or both of jaws (622, 624) includes one or more electrodes that is/are operable to apply RF energy to tissue as described herein. In addition, or in the alternative, end effector (620) may include an ultrasonic blade and/or various other features. Segments (612, 614) may be operable to pivot relative to shaft (610) and relative to each other to thereby deflect end effector (620) laterally away from or toward the central longitudinal axis of shaft (610).

Instrument (600) of this example further includes a first wire set (630) spanning through shaft (610), a second wire set (632) spanning through shaft (610) and both segments (612, 614), and a third wire set (634) spanning further through shaft (610) and both segments (612, 614). Wire sets (630, 632, 634) may be operable to control movement of segments (612, 614) relative to shaft (610). For instance, power may be communicated along one or more of wire sets (630, 632, 634) to selectively engage or disengage corresponding clutching mechanisms, to thereby allow lateral deflection of one or both of segments (612, 614) relative to shaft (610); and or rotation of one or both of segments (612, 614) relative to shaft (610). Alternatively, power may be communicated along one or more of wire sets (630, 632, 634) to drive corresponding solenoids, motors, or other features to actively drive lateral deflection of one or both of segments (612, 614) relative to shaft (610); and or rotation of one or both of segments (612, 614) relative to shaft (610). In versions where end effector (620) is operable to apply RF energy to tissue, one or more additional wires may extend along shaft (610) and segments (612, 614), in addition to wire sets (630, 632, 634).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/ or electrically conductive mechanical features that may provide a risk of generating electrical potentials between proximate components or creating capacitive couplings between electrical features and/or between an electrical feature and an electrically conductive mechanical feature. In the context of instrument (600), such risks may occur with respect to wire sets (630, 632, 634), the electrical components that wire sets (630, 632, 634) are coupled with, and/or other features that drive lateral deflection of one or both of segments (612, 614) relative to shaft (610). In addition, instrument (600) may include one or more sensors in shaft assembly (610) and/or end effector (620); and may also include one or more electrodes and/or other electrical features in end effector (620). Other components of instrument (600) that may present the above-described risks will be apparent to those skilled in the art in view of the teachings herein.

F. Example of Sensors in Shaft Assembly

Figure 10:
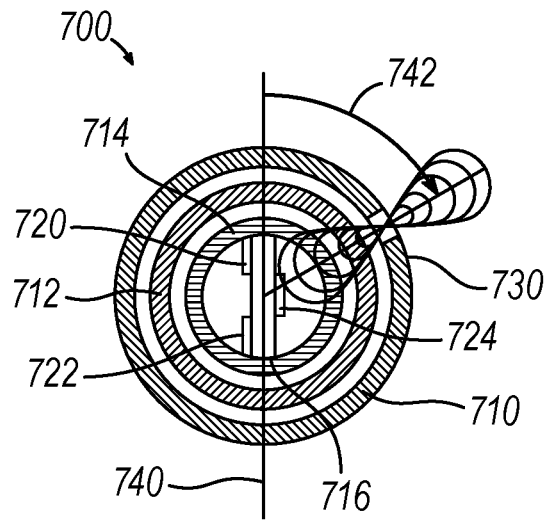
FIG. 10 depicts a cross-sectional end view of another shaft assembly that may be incorporated into a surgical instrument.

FIG. 10 shows an example of another shaft assembly (700) that may be incorporated into any of the various instruments (40, 50, 60, 100, 190, 200, 300, 350, 400, 500, 600) described herein. In addition to the following teachings, shaft assembly (700) may be constructed and operable in accordance with at least some of the teachings of U.S. Pub. No. 2017/0202608, issued as U.S. Pat. No. 10,835,307 on Nov. 17, 2020, the disclosure of which is incorporated by reference herein, in its entirety; and/or various other references cited herein. Shaft assembly (700) of this example includes an outer shaft (710), a first inner shaft (712), and a second inner shaft (714). A support member (716) spans diametrically across the interior of second inner shaft (714).

By way of example only, support member (716) may comprise a circuit board, a flex-circuit, and/or various other electrical components. A plurality of sensors (720, 722, 724) are positioned on support member (716) in the present example. A magnet (730) is embedded in outer shaft (710) which is operable to rotate about inner shafts (712, 714).

In some versions, rotation of outer shaft (710) about inner shafts (712, 714) drives rotation of an end effector (not shown), located at the distal end of shaft assembly (700), about a longitudinal axis of shaft assembly (700). In some other versions, rotation of outer shaft (710) about inner shafts (712, 714) drives lateral deflection of the end effector away from or toward the longitudinal axis of shaft assembly (700). Alternatively, rotation of outer shaft (710) about inner shafts (712, 714) may provide any other results. In any case, sensors (720, 722, 724) may be configured to track the position of magnet (730) and thereby determine a rotational position (742) of outer shaft (710) relative to a fixed axis (740). Thus, sensors (720, 722, 724) may collectively serve as a position sensor like position sensor (112) of instrument (100).

Figure 11:
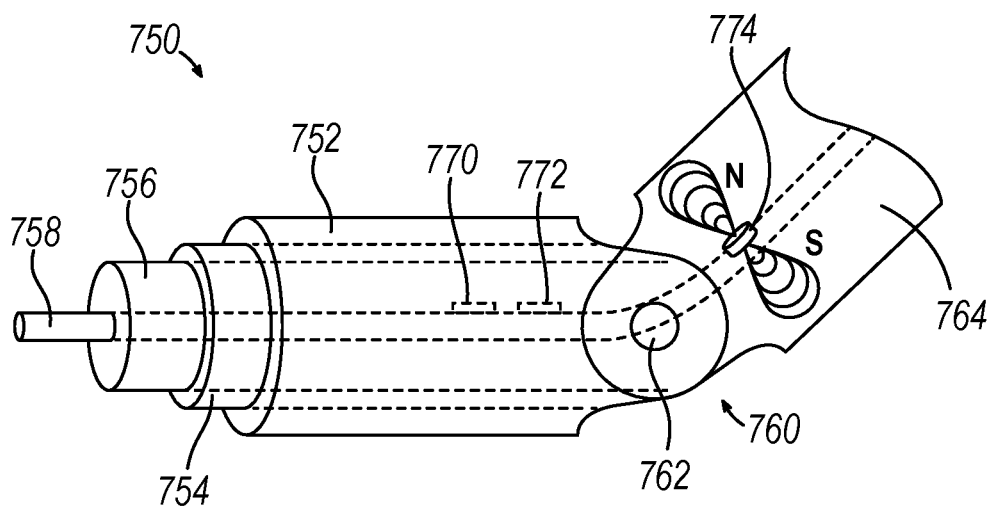
FIG. 11 depicts a schematic view of a portion of another shaft assembly that may be incorporated into a surgical instrument.

FIG. 11 shows an example of another shaft assembly (750) that may be incorporated into any of the various instruments (40, 50, 60, 100, 190, 200, 300, 350, 400, 500, 600) described herein. In addition to the following teachings, shaft assembly (750) may be constructed and operable in accordance with at least some of the teachings of U.S. Pub. No. 2017/0202608, issued as U.S. Pat. No. 10,835,307 on Nov. 17, 2020, the disclosure of which is incorporated by reference herein, in its entirety; and/or various other references cited herein. Shaft assembly (750) of this example includes a plurality of coaxially positioned proximal shaft segments (752, 754, 756) and a distal shaft segment (764). Distal shaft segment (764) is pivotably coupled with proximal shaft segment (752) via a pin (762) to form an articulation joint (760). An end effector (not shown) may be positioned distal to distal shaft segment (764), such that articulation joint (760) may be utilized to deflect the end effector laterally away from or toward a central longitudinal axis defined by proximal shaft segments (752, 754, 756). A flex circuit (758) spans along shaft segments (752, 754, 756, 764) and is operable to flex as shaft assembly (750) bends at articulation joint (760).

A pair of sensors (770, 772) are positioned along flex circuit (758) within the region that is proximal to articulation joint (760); while a magnet (774) is positioned on flex circuit (758) (or elsewhere within distal shaft segment (764)) in the region that is distal to articulation joint (760). Magnet (774) thus moves with distal shaft segment (764) as distal shaft segment (764) pivots relative to proximal shaft segments (752, 754, 756) at articulation joint (760); while sensors (770, 772) remain stationary during such pivoting. Sensors (770, 772) are configured to track the position of magnet (774) and thereby determine a pivotal position of distal shaft segment (764) relative to proximal shaft segments (752, 754, 756). In other words, sensors (770, 772) and magnet (774) cooperate to enable determination of the articulation bend angle formed by shaft assembly (750). Thus, sensors (770, 772) may collectively serve as a position sensor like position sensor (112) of instrument (100).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/ or electrically conductive mechanical features that may provide a risk of generating electrical potentials between proximate components or creating capacitive couplings between electrical features and/or between an electrical feature and an electrically conductive mechanical feature. In the context of instruments (700, 750), such risks may occur with respect to sensors (720, 722, 724, 770, 772), the electrical components that sensors (720, 722, 724, 770, 772) are coupled with, and/or other features within the shaft assemblies of instruments (700, 750). Other components of instruments (700, 750) that may present the above-described risks will be apparent to those skilled in the art in view of the teachings herein.

G. Example of Drive Controls in Body and Shaft Assembly of Instrument

Figure 12:
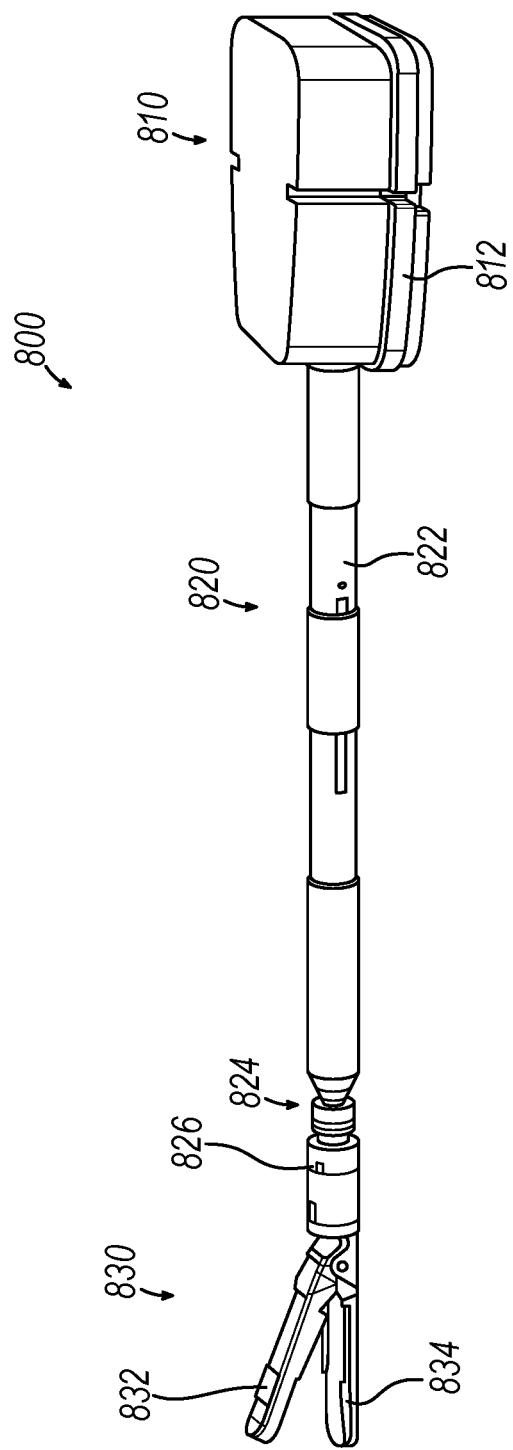
FIG. 12 depicts a perspective view of an example of a surgical instrument that may be incorporated into the robotic surgical system of FIG. 1.
Figure 13:
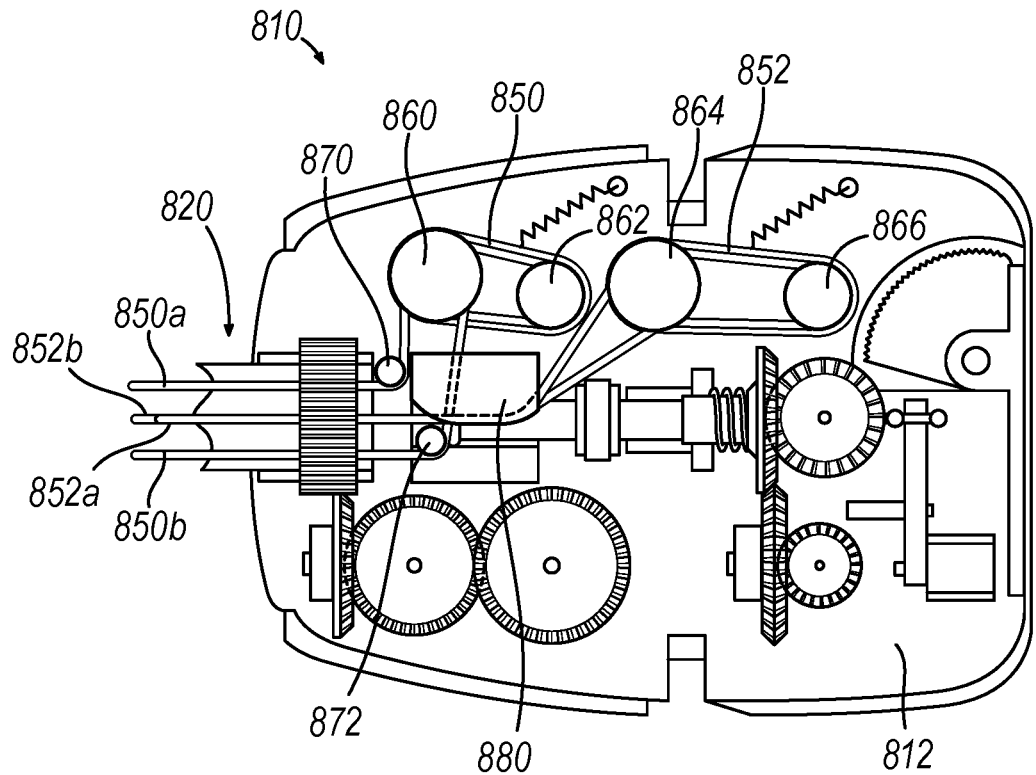
FIG. 13 depicts a top plan view of an interface drive assembly of the instrument of FIG. 12.
Figure 14:
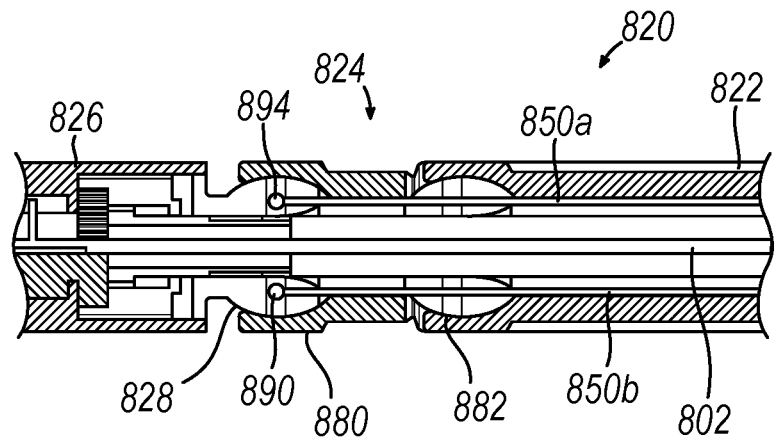
FIG. 14 depicts a cross-sectional side view of an articulation section of a shaft assembly of the instrument of FIG. 12.

FIGS. 12-14 show an example of an instrument (800) that may be incorporated into a robotic surgical system, such as the robotic surgical systems (10, 150) described herein. In addition to the following teachings, instrument (800) may be constructed and operable in accordance with at least some of the teachings of U.S. Pat. No. 9,125,662, the disclosure of which is incorporated by reference herein, in its entirety; and/or various other references cited herein. Instrument (800) of this example includes a body (810), a shaft assembly (820), and an end effector (830). Body (810) includes a base (812) that is configured to couple with a complementary component of a robotic arm (e.g., one of robotic arms (160, 170, 180)). Shaft assembly (820) includes a rigid proximal portion (822), an articulation section (824), and a distal portion (826). End effector (830) is secured to distal portion (826). Articulation section (824) is operable to deflect distal portion (826) and end effector (830) laterally away from and toward the central longitudinal axis defined by proximal portion (822). End effector (830) of this example includes a pair of jaws (832, 834). By way of example only, end effector (830) may be configured and operable like any of the various end effectors (46, 56, 66, 102, 230, 320, 350, 620) described herein.

As shown in FIGS. 13-14, a plurality of drive cables (850, 852) extend from body (810) to articulation section (824) to drive articulation of articulation section (824). Cable (850) is wrapped around a drive pulley (862) and a tensioner (860). Cable (850) further extends around a pair of guides (870, 872), such that cable (850) extends along shaft assembly (820) in two segments (850a, 850b). Cable (852) is wrapped around a drive pulley (866) and a tensioner (864). Cable (852) further extends around a guide (880), such that cable (852) extends along shaft assembly (820) in two segments (852a, 852b). In the present example, each drive pulley (862, 866) is configured to couple with a corresponding drive member (e.g., drive spindle, etc.) of the component of the robotic arm to which base (812) is secured. When drive pulley (862) is rotated, one segment (850a) of cable (850) will translate in a first longitudinal direction along shaft assembly (820); while the other segment (850b) will simultaneously translate in a second (opposite) direction along shaft assembly (820). Similarly, when drive pulley (866) is rotated, one segment (852a) of cable (852) will translate in a first longitudinal direction along shaft assembly (820); while the other segment (852b) will simultaneously translate in a second (opposite) direction along shaft assembly (820).

As shown in FIG. 14, articulation section (824) of the present example includes an intermediate shaft segment (880) that is longitudinally interposed between proximal portion (822) and distal portion (826). A ball feature (828) at the proximal end of distal portion (826) is seated in a socket at the distal end of intermediate shaft segment (880), such that distal portion (826) is operable to pivot relative to intermediate shaft segment (880) along one or more planes. Segments (850a, 850b) of drive cable (850) terminate in corresponding ball-ends (894, 890), which are secured to ball feature (828) of distal portion (822). Drive cable (850) is thus operable to drive pivotal movement of distal portion (826) relative to intermediate shaft segment (880) based on the direction in which drive pulley (862) rotates. A ball feature (882) at the proximal end of intermediate portion (880) is seated in a socket at the distal end of proximal portion (822), such that intermediate portion (880) is operable to pivot relative to proximal portion (822) along one or more planes. In some versions, this pivotal movement of intermediate portion (880) relative to proximal portion (822) is driven by cable (852). As also shown in FIG. 14, an electrical cable (802) passes through articulation section (824). Electrical cable (802) provides a path for electrical communication to end effector (830), thereby allowing for delivery of electrical power (e.g., RF energy) to one or more electrodes in end effector (830), providing a path for electrical signals from one or more sensors in end effector (830) to be communicated back to body (810), and/or other forms of electrical communication.

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (800), such risks may occur with respect to drive cables (850, 852), the components that (850, 852) are coupled with, electrical features within shaft assembly (820), and/or other features within instrument (800). Other components of instrument (800) that may present the above-described risks will be apparent to those skilled in the art in view of the teachings herein.

Figure 15:
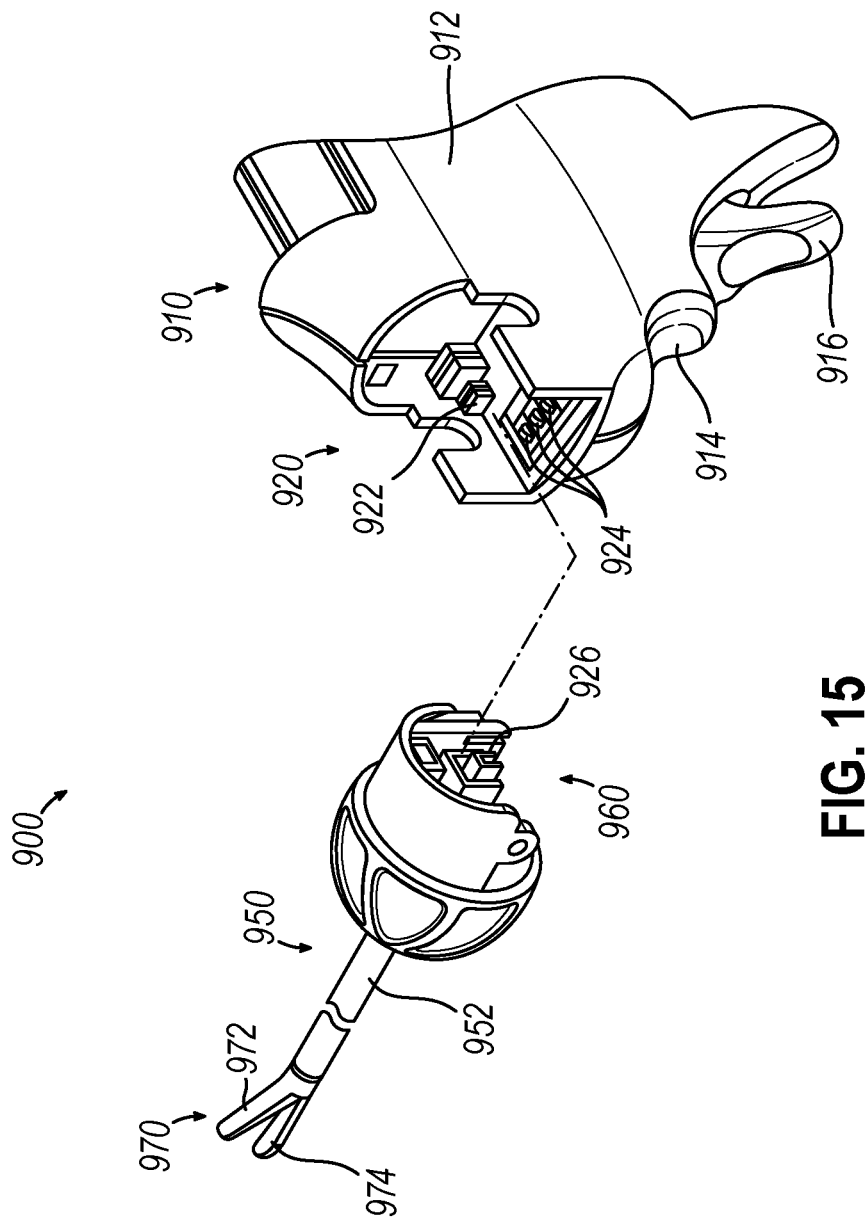
FIG. 15 depicts a perspective view of another example of a handheld surgical instrument, with a modular shaft assembly separated from a handle assembly.

H. Example of Electrical Features at Interface Between Modular Components of Instrument In some instances, it may be desirable to provide a surgical instrument that allows for modular coupling and decoupling of components. For instance, FIG. 15 shows an example of an instrument (900) that includes a handle assembly (910) and a modular shaft assembly (950). While instrument (900) of this example is handheld, similar features and modularity may be readily incorporated into a robotically controlled instrument. Handle assembly (910) of this example includes a body (912), an activation button (914), a pivoting trigger (916), and a shaft interface assembly (920). Shaft interface assembly (920) includes a mechanical drive feature (922) and an array of electrical contacts (924). Electrical contacts (924) may be in electrical communication with a control circuit, power source, and/or various other electrical features within handle assembly (910) as will be apparent to those skilled in the art in view of the teachings herein.

Shaft assembly (950) includes a shaft section (952) and an end effector (970), which includes a pair of jaws (972, 874). Shaft section (952) and end effector (970) may be configured and operable in accordance with any of the various shaft assemblies and end effectors described herein. Shaft assembly (950) of this example further includes a handle interface assembly (960). Handle interface assembly (960) includes a mechanical drive feature (962) and a plurality of electrical contacts (not shown). These electrical contacts of handle interface assembly (960) may be in electrical communication with one or more electrodes, sensors, and/or other electrical components within shaft section (952) and/or end effector (970) as will be apparent to those skilled in the art in view of the teachings herein.

When shaft assembly (950) is coupled with handle assembly (910), mechanical drive feature (922) of handle assembly (910) mechanically couples with mechanical drive feature (962) of shaft assembly (950), such that mechanical drive features (922, 962) may cooperate to communicate motion from a motive power source in handle assembly (910) (e.g., pivoting trigger (916), a motor, etc.) to one or more components within shaft section (952) and, in some versions, end effector (970). In some versions, mechanical drive features (922, 962) cooperate to communicate rotary motion from a motive power source in handle assembly (910) (e.g., pivoting trigger (916), a motor, etc.) to one or more components within shaft section (952) and, in some versions, end effector (970). In addition, or in the alternative, mechanical drive features (922, 962) may cooperate to communicate linear translational motion from a motive power source in handle assembly (910) (e.g., pivoting trigger (916), a motor, etc.) to one or more components within shaft section (952) and, in some versions, end effector (970).

When shaft assembly (950) is coupled with handle assembly (910), electrical contacts (924) of shaft interface assembly (920) also couple with complementary electrical contacts of handle interface assembly (960), such that these contacts establish continuity with each other and thereby enable the communication of electrical power, signals, etc. between handle assembly (910) and shaft assembly (950). In addition to or in lieu of having contacts (924), electrical continuity may be provided between handle assembly (910) and shaft assembly (950) via one or more electrical couplings at mechanical drive features (922, 962). Such electrical couplings may include slip couplings and/or various other kinds of couplings as will be apparent to those skilled in the art in view of the teachings herein.

In some scenarios where electrical power or electrical signals are communicated across mating contacts that provide electrical continuity between two components of an instrument (e.g., contacts (924) of shaft interface assembly (920) and complementary electrical contacts of handle interface assembly (960)), there may be a risk of short circuits forming between such contacts. This may be a particular risk when contacts that are supposed to be electrically isolated from each other are located in close proximity with each other, and the area in which these contacts are located may be exposed to fluids during use of the instrument. Such fluid may create electrical bridges between contacts and/or bleed signals that are being communicated between contacts that are supposed to be coupled with each other. It may therefore be desirable to provide features to prevent or otherwise address such occurrences at contacts of an instrument like instrument (900).

In some scenarios where electrical power or electrical signals are communicated across mechanical couplings between different components of an instrument (e.g., via slip couplings, etc.), such couplings might provide variable electrical resistance in a shaft assembly or other assembly of the instrument. For instance, motion at mechanical drive features (922, 962) may provide variable electrical resistance at an electrical slip coupling between mechanical drive features (922, 962); and this variable electrical resistance may impact the communication of electrical power or electrical signals across the slip coupling. This may in turn result in signal loss or power reductions. It may therefore be desirable to provide features to prevent or otherwise address such occurrences at electrical couplings that are found at mechanical couplings between two moving parts of an instrument like instrument (900).

IV. EXAMPLES OF ELECTROSURGICAL INSTRUMENT WITH ELECTRICAL RESISTANCE MONITOR AT ROTARY COUPLING

The following description relates to examples of different features that may be incorporated into any of the various surgical systems described above. Thus, the below-described features may be combined in various permutations as will be apparent to those skilled in the art in view of the teachings herein. Similarly, various ways in which the below-described features may be incorporated into any of the various surgical systems described above will be apparent to those skilled in the art in view of the teachings herein. It should be understood that the below-described features may be incorporated into robotically controlled surgical instruments and/or handheld surgical instruments.

As noted above, some instruments may include joints in a shaft assembly where one component of the shaft assembly articulates relative to another component at a pivot point in the shaft assembly, or where one component of the shaft assembly rotates about a central longitudinal axis relative to another component of the shaft assembly, etc. Examples of rotary coupling joints in a shaft assembly are described above in the context of instrument (600) shown in FIG. 9; while other examples will be apparent to those skilled in the art in view of the teachings herein. Examples of pivoting articulation joints in a shaft assembly are described above in the context of shaft assembly (750) shown in FIG. 11; while other examples will be apparent to those skilled in the art in view of the teachings herein. In versions of instruments with telescoping shaft assembly components, one component of the shaft assembly may translate relative to another component of the shaft assembly to thereby change the effective length of the shaft assembly.

Regardless of whether an instrument includes a rotary joint, a pivoting articulation joint, a telescoping joint, and/or some other kind of joint, it may be necessary to provide electrical communication across such joints. For instance, such electrical communication may include communication of RF power from a console to an end effector via one or more movable joints within a shaft assembly. Such electrical communication may also include providing a common ground return path along the length of the shaft assembly (e.g., from the end effector to the console), with such a ground return path needing to pass through one or more movable joints within a shaft assembly. Such electrical communication may also include communication of signals from a sensor in an end effector or distal portion of a shaft assembly to the console via one or more movable joints within a shaft assembly. Some merely illustrative examples of sensors that may be included in a shaft assembly are described above in the context of shaft assembly (700) shown in FIG. 10 and shaft assembly (750) shown in FIG. 11, though other ways in which sensors may be integrated into a shaft assembly or end effector will be apparent to those skilled in the art in view of the teachings herein. For instance, in end effectors that include electrodes for applying bipolar RF energy to tissue those same electrodes may be used as sensors to sense impedance in tissue that is being contacted by the end effector. Regardless of what the electrical couplings are used for, movable joints of a shaft assembly may include one or more slip couplings (e.g., slip rings and corresponding leaf springs or other sliding contacts, etc.) or other kinds of couplings that are configured to provide electrical continuity across the joint without compromising freedom of movement at the joint.

In some scenarios, the electrical communication properties of electrical couplings at joints as described above may change during use of an instrument. For instance, such electrical couplings may be exposed to tissue debris, saline, bodily fluids, or other fluids during a surgical procedure, as it may be difficult to achieve fluid-tight seals at such joints. When such debris or fluids are conductive or at least semi-conductive, intrusion of such debris or fluids through the joints may ultimately reach the electrical couplings at the joints and thereby contaminate the electrical couplings, which may affect the electrical communication properties of those electrical couplings. This may include affecting the resistance and/or voltage at the joints. This may in turn introduce noise into electrical signals that are communicated across the joints; or in some cases, cause signal loss across the joints. Contamination of an electrical coupling may also create short circuits between contacts, cause heating of the contaminant(s), and/or cause heating of the joint. This undesired heat may cause undesired tissue trauma or other undesired effects in the surgical field, adversely affect operability of the instrument, and/or damage one or more components of the instrument. In some instances, as the electrical resistance at an electrical coupling of a movable joint increases, the heat generated at the electrical coupling increases; such that an increase in the resistance of an electrical coupling of a movable joint may be indicative of the amount of heat generated as an electrical signal or power passes through that electrical coupling.

In view of the foregoing, it may be desirable to monitor changes in electrical properties (e.g., voltage, electrical resistance, etc.) of electrical couplings (e.g., slip couplings, etc.) at movable joints (e.g., rotary couplings, pivoting articulation joints, telescoping joints, etc.) within an instrument; and provide an automated response in real time for changes that are detected. Such responses may include adjustments of generator power levels, signal processing magnitude, etc. In some instances, changes of resistance of the monitored components may result from positional changes (i.e., varied angular orientation of components relative to each other, varied articulation angles, etc.) of the instrument components; and the console may vary the power output during operation based upon the positional changes of certain components if the monitoring determines that an electrical coupling at a joint has become contaminated. Examples of how such monitoring and responding may be carried out are described in greater detail below.

Figure 16:
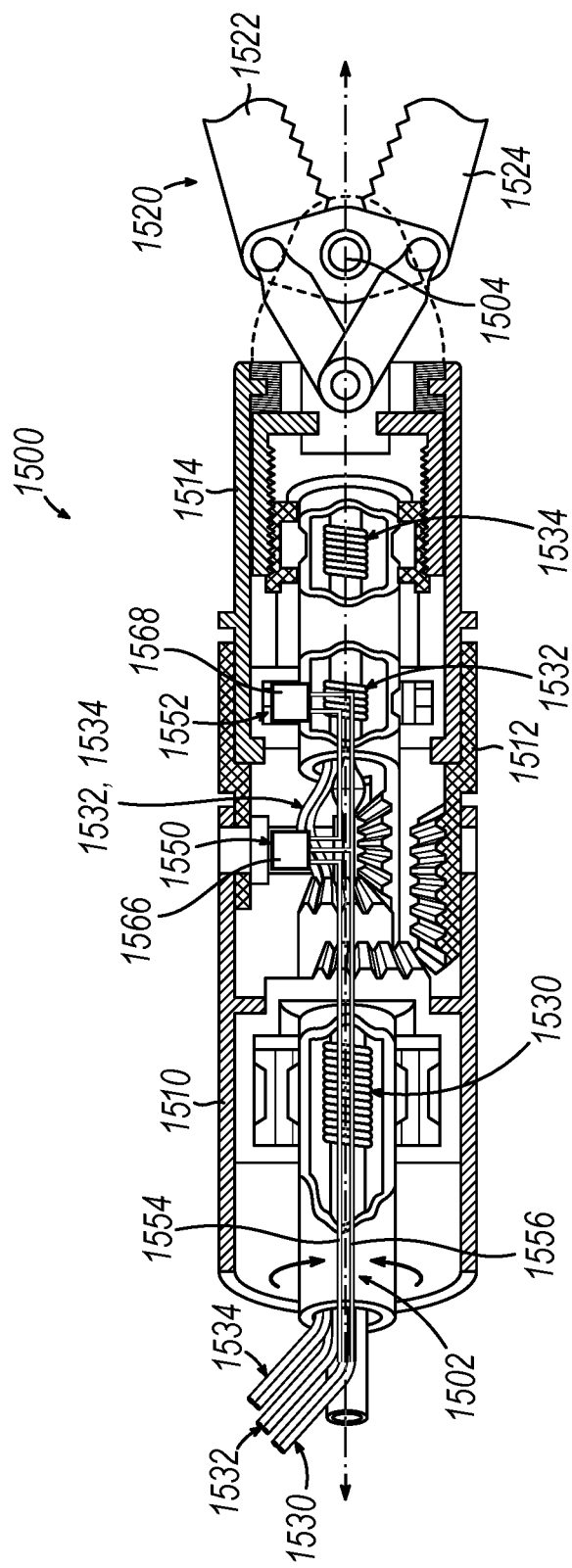
FIG. 16 depicts a side elevation view of a portion of another shaft assembly that may be incorporated into a surgical instrument, with housing components of the shaft being shown in cross-section to reveal internal components of the shaft.

FIG. 16 shows one example of the monitoring system described above. As shown in FIG. 16, an instrument (1500) includes an elongate shaft (1510). While instrument (1500) is illustrated and described in detail, various other electrosurgical instruments have been contemplated including, but not limited to, the instruments described herein above. Instrument (1500) includes a first articulating segment (1512) and a second articulating segment (1514). End effector (1520) is positioned at the distal end of second articulating segment (1514). End effector (1520) of this example includes a pair of jaws (1522, 1524) that are operable to pivot toward and away from each other to grasp tissue. In some versions, one or both of jaws (1522, 1524) includes one or more electrodes that is/are operable to apply RF energy to tissue as described herein. In addition, or in the alternative, end effector (1520) may include an ultrasonic blade and/or various other features.

Segments (1512, 1514) may be operable to pivot relative to shaft (1510) and relative to each other to thereby define joints (1550, 1552), respectively, to provide deflection of end effector (1520) laterally away from or toward the central longitudinal axis (1504) of shaft (1510). In addition, or in the alternative, one or both of segments (1512, 1514) may be operable to rotate relative to shaft (1510) about the central longitudinal axis (1504). Thus, joints (1550, 1552) may constitute pivoting articulation couplings and/or rotary couplings. In either case, joints (1550, 1552) may each include one or more slip couplings or other kinds of electrical couplings that are configured to provide electrical continuity across joints (1550, 1552) without compromising freedom of movement at joints (1550, 1552). Such electrical couplings may provide communication of RF power to end effector (1520), provide a ground return path across joints (1550, 1552), provide communication of electrical signals from one or more sensors in end effector (1520) and/or segments (1512, 1514), and/or provide any other kind of electrical communication.

A console or other processing module of instrument (1500) may receive resistance measurements, voltage measurements, temperature measurements, and/or other kinds of measurements from one or more sensors, as will be described below; and react accordingly to initiate the corrective action. By way of example only, such a console or other processing module may be configured similar to console (20) described above with reference to FIG. 1 or any other console or control circuit described herein; and may include a data processor configured and operable to initiate the corrective action, adjust the power profile sent to instrument (1500), or drain any excess energy stored within instrument (1500). Further, the console or other processing module may be a component of a robotic electrosurgical system, as described above.

Instrument (1500) of this example further includes a first wire set (1530) spanning through shaft (1510), a second wire set (1532) spanning through shaft (1510) and both segments (1512, 1514), and a third wire set (1534) spanning further through shaft (1510) and both segments (1512, 1514). Wire sets (1530, 1532, 1534) may be operable to control movement of segments (1512, 1514) relative to shaft (1510). For instance, power may be communicated along one or more of wire sets (1530, 1532, 1534) to selectively engage or disengage corresponding clutching mechanisms, to thereby allow lateral deflection of one or both of segments (1512, 1514) relative to shaft (1510); and or rotation of one or both of segments (1512, 1514) relative to shaft (1510). Alternatively, power may be communicated along one or more of wire sets (1530, 1532, 1534) to drive corresponding solenoids, motors, or other features to actively drive lateral deflection of one or both of segments (1512, 1514) relative to shaft (1510); and or rotation of one or both of segments (1512, 1514) relative to shaft (1510). One or more additional wires may also provide RF power (bipolar RF and/or monopolar RF) to end effector (1520). In addition, or in the alternative, one or more additional wires may also provide communication of electrical signals from one or more sensors in end effector (1520) and/or segments (1512, 1514).

Moreover, one or more additional wire sets, such as wiring assembly (1502) extends along shaft (1510) in the present example to provide voltage, electrical resistance, temperature, and/or other measurements of joints (1550, 1552) to the console or other processing module. Wiring assembly (1502) may include a power wire (1554) for sensors (1566, 1568) and a return path wire (1556). Wiring assembly (1502) may have intermediate connections positioned at each joint (1550, 1552), adjacent first articulating segment (1512) and second articulating segment (1514), in order to be able to monitor the voltage, electrical resistance, temperature, and/or other parameter(s) of the joint (1550, 1552). As shown, wiring assembly (1502), or alternatively, a flexible circuit, connects integrated sensors (1566, 1568) to monitor variances in the voltage, electrical resistance, temperature, and/or other parameter(s) of joints (1550, 1552).

As noted above, contamination by debris or fluid at joints (1550, 1552) may affect electrical communication properties (e.g., resistance, voltage, etc.) of electrical couplings at joints (1550, 1552). By monitoring the electrical communication properties (e.g., resistance, voltage, etc.) at joints (1550, 1552), the console or other processing module may provide real-time comparisons between monitored electrical communication property values and predetermined values or ranges; and provide an automated corrective action or other response in real time when a monitored electrical communication property value deviates from a predetermined value or range. Alternatively, the console or other processing module may provide any other suitable kind of response(s), examples of which are described in greater detail below. If the console or other processing module detects a voltage, electrical resistance, temperature, and/or other parameter change in one of the joints (1550, 1552), the console or other processing module may then decide whether the variance falls within a predetermined deviation range that would indicate a corrective action is warranted.

By way of example only, the above-described monitoring at joints (1550, 1552) may be used by the console or other processing module to control the electrical power provided to end effector (1520) based on the variations of voltage, electrical resistance, temperature, and/or other parameter(s) measured adjacent one or more of the joints (1550, 1552). In addition, or in the alternative, the console or other processing module may adapt the resistance provided via return path wire (1556) (e.g., to the resistance of power wire (1554)) to sufficiently bleed-off current to prevent damage to instrument (1500) due to inadvertent electrical short circuits. By monitoring the resistance and/or other electrical parameters at joints (1550, 1552) over time, the console or other processing module could adjust the maximum power limits send to end effector (1520) to prevent instrument (1500) from heating up or becoming damaged. In addition, the generator may selectively increase or decrease power as necessary, based on the above-described monitoring at joints (1550, 1552), to provide a constant or predictable thermal effect at end effector (1520).

In addition to monitoring electrical parameters at joints (1550, 1552), or as an alternative to monitoring electrical parameters at joints (1550, 1552), sensors (1566, 1568) may monitor temperature at joints (1550, 1552). By monitoring temperature at joints (1550, 1552), with or without monitoring of electrical parameters at joints (1550, 1552), the console or other processing module may further tune the delivery of power (e.g., bipolar RF, monopolar RF, etc.) to end effector (1520) without creating excessive heat at joint (1550, 1552) that might otherwise cause undesired tissue trauma or other undesired effects in the surgical field, adversely affect operability of instrument (1500), and/or damage one or more components of instrument (1500) at or near joint (1550, 1552). By way of example only, a generator may adjust the frequency or maximum duty cycle of the applied energy rather than merely adjusting the power level, in response to the monitored temperature of joint (1550, 1552) exceeding a predetermined threshold value.

While the foregoing examples are described in the context of contaminants reaching electrical connections via joints (1550, 1552) and having undesired electrical and/or thermal effects, the normal operation of instrument (1500) may also eventually create undesired electrical and/or thermal effects at electrical connections of joints (1550, 1552) (even in the absence of contaminants in joints (1550, 1552). For instance, communication of bipolar RF energy or monopolar RF energy through electrical connections (e.g., slip couplings, etc.) at joints (1550, 1552) may result in heating up of those electrical connections. Such heating may represent a power loss, such that the RF electrode(s) at end effector (1520) is/are not receiving the appropriate amount of power. In such scenarios, where sensors (1566, 1568) pick up on such heat-based losses, the console or other processing module may incrementally increase the level of power delivered from the generator, as needed based on the monitored parameters at joints (1550, 1552), to provide predictable and user-expected results on the tissue being engaged by end effector (1520). For instance, these results may include predictable and user-expected tissue sealing, ablation, etc.

While it may be appropriate to incrementally increase the level of power delivered from the generator to compensate for heat losses at joints (1550, 1552), the process may reach a point where this kind of response is no longer feasible. For instance, increasing the power level beyond a certain point may result in damage to instrument (1500), erratic or undesired tissue effects from end effector (1520), unreliable feedback from one or more sensors of instrument (1500), and/or other undesired effects. Thus, the console or other processing module may incrementally increase the level of power delivered from the generator as one or more monitored parameters at joints (1550, 1552) change through a certain range; but then provide a different kind of response once the one or more monitored parameters at joints (1550, 1552) exceed a predetermined threshold value. For instance, in the event that a monitored parameter at one or both of joints (1550, 1552) exceeds a predetermined threshold value (e.g., a maximum electrical resistance value, a maximum temperature value, etc.), the console or other processing module may provide a corrective action.

In some versions, the corrective action includes transitioning instrument (1500) into a "limp mode," which is an alternative mode of operation. By way of example only, a "limp mode" may allow some continued use of instrument (1500), though the console or other processing module may begin to decrease the power to keep the problematic joint (1550, 1552) under a maximum temperature (e.g., to prevent catastrophic failure of the problematic joint (1550, 1552), to prevent the problematic joint (1550, 1552) from burning tissue in the surgical field, etc.). Such a decrease in power may at least temporarily adversely affect the ability of end effector (1520) to impart desired RF effects on tissue. Thus, in the event that the console or other processing module determines that a "limp mode" or other alternative operation mode is warranted in view of a monitored parameter at one or both of joints (1550, 1552) exceeding a predetermined threshold value, the console or other processing module may provide the operator with an alert (e.g., audible, visual, tactile, etc.) to thereby notify the operator that the operation mode of instrument (1500) is changing. This may allow the operator to adjust their surgical technique accordingly, which may include deactivating RF power at least momentarily to allow the problematic joint (1550, 1552) to cool down. The operator may also wish to clean or replace instrument (1500) in response to receiving a "limp mode" alert.

In some versions, sensors (1566, 1568) of instrument (1500) may be configured to monitor the resistance or voltage over time of joints (1550, 1552) and to adjust the power signals or control responses based upon deviations beyond the expected range, as an effect from the outside voltage or potential, to create an offset for the power signal. As joints (1550, 1552) become contaminated, the resistance of electrical couplings within joints (1550, 1552) may change, as noted above. This may introduce electrical noise into the power signal or sensor signal(s); or in some instances, signal loss. If a local alternating load is introduced as a measure of the change of the overall system resistance, sensors (1566, 1568) could be adjusted to compensate for the presence of the contamination.

In some versions, instrument (1500) includes one or more operational parameter sensors (other than sensors (1566, 1568)) that is/are operable to sense various operational parameters associated with instrument (1500). Such operational parameters may include, but are not limited to, position or orientation information about one or more components of instrument (1500), electrical or thermal properties of tissue that is being engaged by end effector (1520), etc. Some merely illustrative examples of position or orientation sensors that may be included in a shaft assembly are described above in the context of shaft assembly (700) shown in FIG. 10 and shaft assembly (750) shown in FIG. 11. As another merely illustrative example, end effector (1520) may include electrodes for applying bipolar RF energy to tissue; and those same electrodes may be used as sensors to sense impedance in tissue that is being contacted by end effector (1520). Other ways in which operational parameter sensors may be integrated into a shaft assembly or end effector, and other operational parameters that may be sensed by such operational parameter sensors, will be apparent to those skilled in the art in view of the teachings herein. Contamination at joints (1550, 1552) may adversely affect the signals from such operational parameter sensors, such as by introducing noise to such signals or otherwise compromising the trustworthiness of the signals from such operational parameter sensors.

Regardless of the location or specific operational parameter(s) sensed by such an operational parameter sensor, a console or other processing module may vary its handling of signals from such an operational parameter sensor based at least in part on feedback from sensors (1566, 1568) indicating contamination at joints (1550, 1552) or other conditions that might adversely affect signals from operational parameter sensors. For instance, in the event that data from one or both of sensors (1566, 1568) indicates a value (e.g., voltage, resistance, etc.) exceeding a first threshold value, such that the signal from a primary operational parameter sensor is being somewhat affected, the console or other processing module may continue to factor in the signal from the affected primary operational parameter sensor as part of the control algorithm; but further rely on signals from one or more secondary operational parameter sensors to execute the control algorithm. In some such scenarios, the signals from the one or more secondary operational parameter sensors may be signals that the console or other processing module would typically not factor in as part of the control algorithm in the absence of the primary operational parameter sensor being affected; such that the signals from the one or more secondary operational parameter sensors are only being factored into the control algorithm because the signals from sensors (1566, 1568) indicate that the signal from the primary operational parameter sensor might be noisy or otherwise somewhat inaccurate. Thus, in this scenario, the affected primary operational parameter sensor may still influence the control algorithm, but the signal from the affected primary operational parameter sensor is now being supplemented by signals from one or more secondary operational parameter sensors.

In the event that data from one or both of sensors (1566, 1568) indicates a value (e.g., voltage, resistance, etc.) exceeding a second threshold value, such that the signal from a primary operational parameter sensor is being substantially affected, the console or other processing module may begin to disregard signals from the primary operational parameter sensor. In other words, the console or other processing module may pause adjustments to components (e.g., a generator, etc.) whose output would otherwise be adjusted in response to signals from the affected primary operational parameter sensor. Alternatively, in conditions where the console or other processing module has begun to disregard signals from the primary operational parameter sensor, the console or other processing module may again start relying on signals from one or more secondary operational parameter sensors to drive the control algorithm (i.e., as a substitute for the now-disregarded signal from the primary operational parameter sensor). The signals from the one or more secondary operational parameter sensors may thus serve as a proxy for the signal from the primary operational parameter sensor. In such scenarios, the one or more secondary operational parameter sensors may sense parameters that are related to, but different from, the parameter sensed by the primary operational parameter sensor. Alternatively, the console or other processing module may apply some other predetermined control algorithm to the outputs of components that would otherwise be adjusted based on signals from the affected operational parameter sensor.

In one merely illustrative example of an instrument having a primary operational parameter sensor and a secondary operational parameter sensor, the instrument includes an end effector with a sensor that senses density or other properties of tissue clamped between jaws of the end effector. This may serve as the primary operational parameter sensor. The electrical signal path between this primary operational parameter sensor in the end effector and a corresponding control module may include a rotary slip coupling in a distal portion of the shaft assembly of the instrument. The instrument may also include a translating knife member that severs tissue captured between the jaws of the end effector. The knife member may be driven by a motor. The control algorithm for the motor may factor in the density or other properties of tissue clamped between jaws of the end effector, such that the control algorithm factors in the signal from the primary operational parameter sensor in the end effector. In the event that a signal from a separate sensor that monitors parameter associated with the slip coupling (e.g., similar to sensors (1566, 1568)) indicates a value (e.g., voltage, resistance, etc.) exceeding a second threshold value, thereby indicating contamination of the slip coupling, and thereby indicating that the signal from the primary operational parameter sensor in the end effector is no longer necessarily reliable, the control module may turn to a secondary operational parameter sensor for a signal to either supplement the signal from the primary operational parameter sensor or substitute the signal from the primary operational parameter sensor. In this example, the secondary operational parameter sensor may include a motor current sensor that is operable to sense the current being used to drive the motor, which is driving the knife member. Since the movement of the knife member may vary based on the properties of the tissue clamped between the jaws of the end effector, the signal from the motor current sensor may serve as an adequate proxy for the signal from the primary operational parameter sensor in the end effector.

In the event that a control module begins to factor signals from a secondary operational parameter sensor into a control algorithm, as a supplement or substitute for signals from a primary operational parameter sensor, based on data from one or both of sensors (1566, 1568) indicating a value (e.g., voltage, resistance, etc.) exceeding a threshold value, such that the signal from a primary operational parameter sensor is being adversely affected, the console or other processing module may continue monitoring data from one or both of sensors (1566, 1568). In some such scenarios, the data from one or both of sensors (1566, 1568) may indicate that the corresponding monitored value (e.g., voltage, resistance, etc.) is no longer exceeding the threshold value, such that the signal from the primary operational parameter sensor is no longer being adversely affected. This may occur, for example, when a contaminant has been worked out of a joint (1550, 1552) during use of instrument (1500). If this occurs, then the control module may turn back to signals from the primary operational parameter sensor to drive the control algorithm; and may stop factoring signals from the one or more secondary operational parameter sensors into the control algorithm.

In some instances, the variation of electrical resistance at slip couplings in joints (1550, 1552) may also provide feedback indicating the level of torque that is being applied at joints (1550, 1552). As another merely illustrative alternative, the variation of electrical resistance at slip couplings in joints (1550, 1552) may also provide feedback indicating the angular positioning of components at joints (1550, 1552). For instance, in a version where a joint (1550, 1552) includes a slip coupling circular race that is terminated at one angle (e.g., 5 degrees), and then the resistance value drops off at a corresponding rotation angle (e.g., 175 degrees), then as the coupling is rotated the resistance within the track may change. This additional loss of resistance may be tracked over time and may be used to not only compensate for the loss and turn it off if it is too great; but also to determine what angle the slip coupling is with respect to the other side of the coupling.

Figure 17:
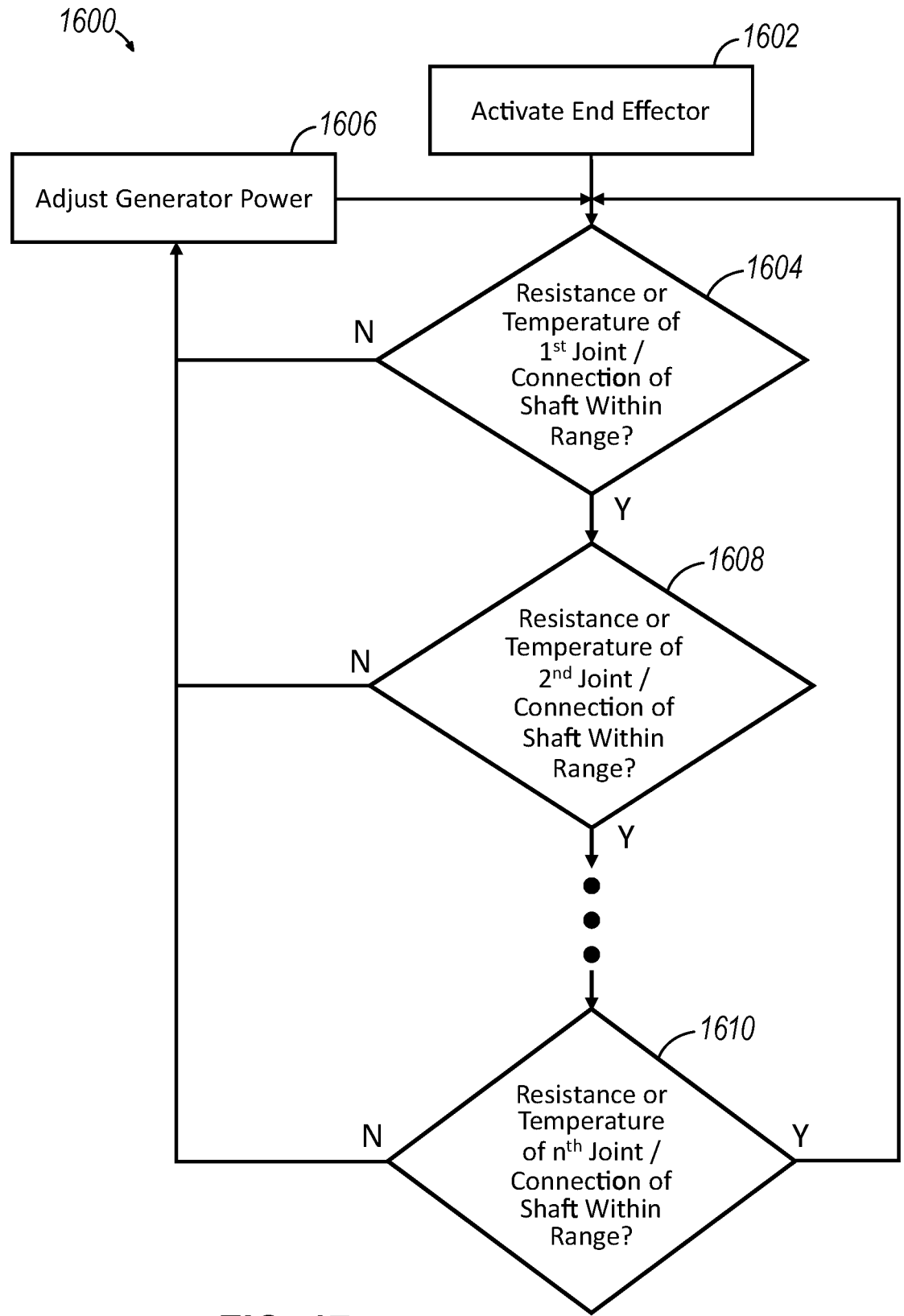
FIG. 17 depicts a flowchart of an exemplary method of monitoring characteristics of mechanical components of a surgical instrument that is operable to apply RF energy to tissue.

FIG. 17. depicts a flowchart of an exemplary method (1600) of monitoring temperature and resistance at couplings of a surgical instrument, as described above. While temperature and resistance are monitored in the present example, any other suitable parameters (e.g., voltage, etc.) may be monitored, in addition to or in lieu of monitoring temperature and/or resistance. At step (block 1602), the system or operator initiates the power output to the end effector from the power generator. During operation, at step (block 1604), sensors (1566, 1568) measure the resistance and temperature at one joint, such as one of joints (1550, 1552), and determines if the measured resistance and temperature variations from normal are within a predetermined range. If the resistance and temperature variations from normal are not within a predetermined range, the sensor transmits a signal back to the console; and at step (block 1606), the console adjusts the generator output power accordingly. Alternatively, in some versions, the console stores known normal resistance and temperature values and the sensor is configured to continuously measure and transmit measured resistance and temperature values to the console. In some such scenarios, the console makes the determination regarding whether the resistance and temperature variations from normal are within a predetermined range.

If the resistance and temperature variations from normal are within a predetermined range at step (block 1604), the method moves to the next one of joints (1550, 1552) to make the same measurement and determination at step (block 1608). If the resistance and temperature variations from normal are not within a predetermined range, the sensor transmits a signal back to the console; and again at step (block 1606), the console adjusts the generator output power accordingly. Thereafter, at step (block 1610), each additional joint is measured and the corrective action made according to the same method as the joints of steps (block 1604, block 1608).

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a shaft assembly, the shaft assembly including: (i) a first shaft component, (ii) a second shaft component, (iii) a joint joining the first shaft component with the second shaft component, the second shaft component being movable relative to the first shaft component at the joint, and (iv) a sliding electrical coupling at the joint, the sliding electrical coupling being configured to provide electrical continuity between the first and second shaft components while permitting movement of the second shaft component relative to the first shaft component at the joint; (b) an end effector positioned at a distal end of the shaft assembly, wherein the end effector is operable to engage tissue of a patient; (c) a control module operable to power the end effector; (d) a first sensor positioned adjacent to the joint, wherein the first sensor is configured to: (i) measure a joint parameter indicating a state of the sliding electrical coupling, and (ii) transmit a first signal indicative of the measured joint parameter to the control module; wherein the control module is configured to: (i) determine whether the measured joint parameter exceeds a maximum deviation from a predetermined value, and (ii) when the measured joint parameter exceeds a maximum deviation from a predetermined value, initiate a first responsive action.

Example 2

The apparatus of Example 1, wherein the shaft assembly defines a longitudinal axis, wherein the second shaft component is rotatable relative to the first shaft component about the longitudinal axis at the joint.

Example 3

The apparatus of any one or more of Examples 1 through 2, wherein the first responsive action includes increasing a power signal provided by the control module to the end effector.

Example 4

The apparatus of any one or more of Examples 1 through 3, wherein the first responsive action includes decreasing a power signal provided by the control module to the end effector.

Example 5

The apparatus of any one or more of Examples 1 through 4, further comprising a second sensor, the second sensor being operable to: (i) measure a first operational parameter associated with operation of the end effector, and (ii) transmit a second signal indicative of the measured first operational parameter to the control module, wherein the control module is configured to execute a control algorithm based at least in part on the second signal.

Example 6

The apparatus of Example 5, wherein the first responsive action includes adjusting a signal processing magnitude of the second signal transmitted by the second sensor while executing the control algorithm.

Example 7

The apparatus of any one or more of Examples 5 through 6, further comprising a third sensor, the third sensor being operable to: (i) measure a second operational parameter associated with operation of the end effector, and (ii) transmit a third signal indicative of the measured second operational parameter to the control module, wherein the first responsive action includes supplementing the second signal with the third signal while executing the control algorithm.

Example 8

The apparatus of any one or more of Examples 5 through 6, further comprising a third sensor, the third sensor being operable to: (i) measure a second operational parameter associated with operation of the end effector, and (ii) transmit a third signal indicative of the measured second operational parameter to the control module, wherein the first responsive action includes substituting the second signal with the third signal while executing the control algorithm.

Example 9

The apparatus of any one or more of Examples 1 through 6, further comprising a third sensor, the third sensor being operable to: (i) measure a second operational parameter associated with operation of the end effector, and (ii) transmit a third signal indicative of the measured second operational parameter to the control module, wherein the control module is configured to disregard the third signal while executing the control algorithm when the measured joint parameter does not exceed the maximum deviation from a predetermined value.

Example 10

The apparatus of any one or more of Examples 1 through 9, the joint parameter indicating an electrical resistance of the sliding electrical coupling.

Example 11

The apparatus of Example 10, the predetermined value being an electrical resistance value associated with a predetermined maximum temperature value.

Example 12

The apparatus of any one or more of Examples 1 through 11, the joint parameter indicating a voltage of the sliding electrical coupling.

Example 13

The apparatus of any one or more of Examples 1 through 12, the joint parameter indicating a temperature of the sliding electrical coupling.

Example 14

The apparatus of any one or more of Examples 1 through 13, further comprising an orientation sensor configured to sense a change of orientation at the joint, wherein the control module is configured to correlate a change of orientation as sensed by the orientation sensor with the measured joint parameter and determine whether to initiate an alternative operation mode.

Example 15

The apparatus of Example 14, wherein the alternative operation mode includes configuring the control module to vary the power to the end effector based upon change of orientation at the joint.

Example 16

The apparatus of any one or more of Examples 1 through 15, wherein the first responsive action includes adjusting a maximum power limit of end effector.

Example 17

The apparatus of any one or more of Examples 1 through 16, wherein the end effector is operable to apply RF energy to tissue.

Example 18

The apparatus of any one or more of Examples 1 through 17, wherein the control module is a component of a robotic electrosurgical system.

Example 19

An apparatus, comprising: (a) a shaft assembly, the shaft assembly including: (i) a first shaft component, (ii) a second shaft component, the first and second shaft components together defining a longitudinal axis, (iii) a rotary joint joining the first shaft component with the second shaft component, the second shaft component being rotatable relative to the first shaft component about the longitudinal axis at the rotary joint, and (iv) a sliding electrical coupling at the rotary joint, the sliding electrical coupling being configured to provide electrical continuity between the first and second shaft components while permitting rotation of the second shaft component relative to the first shaft component at the rotary joint; (b) an end effector positioned at a distal end of the shaft assembly, wherein the end effector is operable to engage tissue of a patient; (c) a control module operable to power the end effector; (d) a sensor positioned adjacent to the rotary joint, wherein the sensor is configured to: (i) measure a joint parameter indicating one or more of an electrical resistance of the sliding electrical coupling, a voltage of the sliding electrical coupling, or a temperature of the sliding electrical coupling, and (ii) transmit a signal indicative of the measured joint parameter to the control module; wherein the control module is configured to: (i) determine whether the measured joint parameter exceeds a maximum deviation from a predetermined value, and (ii) when the measured joint parameter exceeds a maximum deviation from a predetermined value, initiate a responsive action.

Example 20

A method of operating a surgical instrument, wherein the surgical instrument includes shaft assembly having first and second shaft components coupled together at a joint, an end effector positioned at a distal end of the shaft assembly, a control module operable to power the end effector, and a sensor positioned adjacent the joint, the method comprising: (a) providing a power signal from the control module to the end effector; (b) measuring, by the sensor, an electrical or thermal parameter at the joint; (c) transmitting a signal indicative of the measured electrical or thermal parameter to the control module; (d) determining, by the control module, whether the electrical or thermal parameter exceeds a maximum deviation from a predetermined electrical or thermal parameter value; and (e) when the electrical or thermal parameter exceeds the maximum deviation from the predetermined electrical or thermal parameter value, adjusting the power signal provided from the control module to the end effector.

VI. MISCELLANEOUS

Versions of the devices described above may have application in conventional medical treatments and procedures conducted by a medical professional, as well as application in robotic-assisted medical treatments and procedures.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 17/136,136, entitled "Filter for Monopolar Surgical Instrument Energy Path," filed Dec. 29, 2020, published as U.S. Pub. No. 2022/0202474 on Jun. 30, 2022, the disclosure of which is incorporated by reference herein. Various suitable ways in which the teachings herein may be combined with the teachings of U.S. Pub. No. 2022/0202474 will be apparent to those of ordinary skill in the art in view of the teachings herein.

In addition to the foregoing, the teachings herein may be readily combined with the teachings of U.S. patent application Ser. No. 17/136,139, entitled "Electrosurgical Instrument System with Parasitic Energy Loss Monitor," filed Dec. 29, 2020, published as U.S. Pub. No. 2022/0202470 on Jun. 30, 2022, the disclosure of which is incorporated by reference herein. Various suitable ways in which the teachings herein may be combined with the teachings of U.S. Pub. No. 2022/02024740 will be apparent to those of ordinary skill in the art in view of the teachings herein.

In addition to the foregoing, the teachings herein may be readily combined with the teachings of U.S. patent application Ser. No. 17/136,141, entitled "Energized Surgical Instrument System with Multi-Generator Output Monitoring," filed Dec. 29, 2020, issued as U.S. Pat No. 11,992,257 on May 28, 2024, the disclosure of which is incorporated by reference herein. Various suitable ways in which the teachings herein may be combined with the teachings of U.S. patent application Ser. No. 11,992,257 will be apparent to those of ordinary skill in the art in view of the teachings herein.

In addition to the foregoing, the teachings herein may be readily combined with the teachings of U.S. patent application Ser. No. 17/136,145, entitled "Electrosurgical Instrument with Shaft Voltage Monitor," filed Dec. 29, 2020, published as U.S. Pub. No. 2022/0202487 on Jun. 30, 2022, the disclosure of which is incorporated by reference herein. Various suitable ways in which the teachings herein may be combined with the teachings of U.S. Pub. No. 2022/0202487 will be apparent to those of ordinary skill in the art in view of the teachings herein.

In addition to the foregoing, the teachings herein may be readily combined with the teachings of U.S. patent application Ser. No. 17/136,158, entitled "Electrosurgical Instrument with Modular Component Contact Monitoring," filed Dec. 12, 2020, the disclosure of which is incorporated by reference herein. Various suitable ways in which the teachings herein may be combined with the teachings of U.S. patent application Ser. No. 17/136,158 will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus, comprising:
   (a) a shaft assembly, the shaft assembly including:
      (i) a first shaft component,
      (ii) a second shaft component,
      (iii) a joint joining the first shaft component with the second shaft component, the second shaft component being movable relative to the first shaft component at the joint, and
      (iv) a sliding electrical coupling at the joint, the sliding electrical coupling being configured to provide electrical continuity between the first and second shaft components while permitting movement of the second shaft component relative to the first shaft component at the joint;
   (b) an end effector positioned at a distal end of the shaft assembly, wherein the end effector is operable to engage tissue of a patient;
   (c) a control module operable to power the end effector; and
   (d) a first sensor positioned adjacent to the joint, wherein the first sensor is configured to:
      (i) measure an electrical parameter of the joint, and
      (ii) transmit a first signal indicative of the measured electrical parameter to the control module;
   wherein the control module is configured to:
      (i) determine whether the measured electrical parameter exceeds a maximum deviation from a predetermined value such that the measured electrical parameter adversely affects an electrical communication property between the first and second shaft components, and
      (ii) when the measured electrical parameter exceeds the maximum deviation from the predetermined value, initiate a responsive action that mitigates the adverse effect of the measured electrical parameter on the electrical communication property between the first and second shaft components.

2. The apparatus of claim 1, wherein the shaft assembly defines a longitudinal axis, wherein the second shaft component is rotatable relative to the first shaft component about the longitudinal axis at the joint.

3. The apparatus of claim 1, wherein the first responsive action includes increasing a power signal provided by the control module to the end effector.

4. The apparatus of claim 1, wherein the first responsive action includes decreasing a power signal provided by the control module to the end effector.

5. The apparatus of claim 1, further comprising a second sensor, the second sensor being operable to:
   (i) measure a first operational parameter associated with operation of the end effector, and
   (ii) transmit a second signal indicative of the measured first operational parameter to the control module,
   wherein the control module is configured to execute a control algorithm based at least in part on the second signal.

6. The apparatus of claim 5, wherein the first responsive action includes adjusting the second signal transmitted by the second sensor while executing the control algorithm.

7. The apparatus of claim 5, further comprising a third sensor, the third sensor being operable to:
   (i) measure a second operational parameter associated with operation of the end effector, and
   (ii) transmit a third signal indicative of the measured second operational parameter to the control module,
   wherein the responsive action includes supplementing the second signal with the third signal while executing the control algorithm.

8. The apparatus of claim 5, further comprising a third sensor, the third sensor being operable to:
   (i) measure a second operational parameter associated with operation of the end effector, and
   (ii) transmit a third signal indicative of the measured second operational parameter to the control module,
   wherein the responsive action includes substituting the second signal with the third signal while executing the control algorithm.

9. The apparatus of claim 5, further comprising a third sensor, the third sensor being operable to:
 (i) measure a second operational parameter associated with operation of the end effector, and
 (ii) transmit a third signal indicative of the measured second operational parameter to the control module,
 wherein the control module is configured to disregard the third signal while executing the control algorithm when the measured electrical parameter does not exceed the maximum deviation from the predetermined value.

10. The apparatus of claim 1, the electrical parameter indicating an electrical resistance of the sliding electrical coupling.

11. The apparatus of claim 1, the electrical parameter indicating a voltage of the sliding electrical coupling.

12. The apparatus of claim 1, further comprising an orientation sensor configured to sense a change of orientation at the joint, wherein the control module is configured to correlate a change of orientation as sensed by the orientation sensor with the measured electrical parameter and determine whether to initiate an alternative operation mode.

13. The apparatus of claim 12, wherein the alternative operation mode includes configuring the control module to vary the power to the end effector based upon change of orientation at the joint.

14. The apparatus of claim 1, wherein the responsive action includes adjusting a maximum power limit of end effector.

15. The apparatus of claim 1, wherein the end effector is operable to apply RF energy to tissue.

16. The apparatus of claim 1, wherein the control module is a component of a robotic electrosurgical system.

17. An apparatus, comprising:
 (a) a shaft assembly, the shaft assembly including:
  (i) a first shaft component,
  (ii) a second shaft component, the first and second shaft components together defining a longitudinal axis,
  (iii) a rotary joint joining the first shaft component with the second shaft component, the second shaft component being rotatable relative to the first shaft component about the longitudinal axis at the rotary joint, and
  (iv) a sliding electrical coupling at the rotary joint, the sliding electrical coupling being configured to provide electrical continuity between the first and second shaft components while permitting rotation of the second shaft component relative to the first shaft component at the rotary joint;
 (b) an end effector positioned at a distal end of the shaft assembly, wherein the end effector is operable to engage tissue of a patient;
 (c) a control module operable to power the end effector; and
 (d) a sensor positioned adjacent to the rotary joint, wherein the sensor is configured to:
  (i) measure an electrical parameter of the rotary joint, the electrical parameter indicating one or more of an electrical resistance of the sliding electrical coupling or a voltage of the sliding electrical coupling, and
  (ii) transmit a signal indicative of the measured electrical parameter to the control module;
 wherein the control module is configured to:
  (i) determine whether the measured electrical parameter exceeds a maximum deviation from a predetermined value that indicates that an electrical communication property between the first and second shaft components has degraded beyond a predefined threshold, and
  (ii) when the measured electrical parameter exceeds the maximum deviation from the predetermined value, initiate a responsive action that improves the electrical communication property between the first and second shaft components.

18. The apparatus of claim 17, the electrical parameter indicating an electrical resistance of the sliding electrical coupling.

19. The apparatus of claim 17, the electrical parameter indicating a voltage of the sliding electrical coupling.

20. A method of operating a surgical instrument, wherein the surgical instrument includes shaft assembly having first and second shaft components coupled together at a joint, an end effector positioned at a distal end of the shaft assembly, a control module operable to power the end effector, and a sensor positioned adjacent the joint, the method comprising:
 (a) providing a power signal from the control module to the end effector;
 (b) measuring, by the sensor, an electrical parameter at the joint;
 (c) transmitting a signal indicative of the measured electrical parameter to the control module;
 (d) determining, by the control module, whether the electrical parameter exceeds a maximum deviation from a predetermined electrical parameter value such that the electrical parameter adversely affects operation of the end effector; and
 (e) when the electrical parameter exceeds the maximum deviation from the predetermined electrical parameter value, adjusting the power signal provided from the control module to the end effector to mitigate the adverse effect of the electrical parameter on the operation of the end effector.

* * * * *